United States Patent
Elliott et al.

(10) Patent No.: US 6,537,192 B1
(45) Date of Patent: Mar. 25, 2003

(54) AUTOMATED RADIOISOTOPE SEED LOADER SYSTEM FOR IMPLANT NEEDLES

(75) Inventors: Daniel M. Elliott, Shorewood, MN (US); George M. Hoedeman, Eden Prairie, MN (US); John J. Berkey, St. Louis Park, MN (US); Jonathan D. Elliott, St. Paul, MN (US)

(73) Assignee: Mentor Corporation, Santa Barbara, CA (US)

( * ) Notice: Subject to any disclaimer, the term of this patent is extended or adjusted under 35 U.S.C. 154(b) by 87 days.

(21) Appl. No.: 09/587,624

(22) Filed: Jun. 5, 2000

(51) Int. Cl.⁷ .............................................. A61M 36/00
(52) U.S. Cl. .......................................................... 600/1
(58) Field of Search ................................ 600/1–8, 427; 604/57, 59–64; 976/DIG. 350; 250/507.1

(56) References Cited

U.S. PATENT DOCUMENTS

| | | |
|---|---|---|
| 4,086,914 A | 5/1978 | Moore |
| 4,150,298 A | 4/1979 | Brault et al. |
| 4,167,179 A | 9/1979 | Kirsch |

(List continued on next page.)

FOREIGN PATENT DOCUMENTS

| | | |
|---|---|---|
| EP | 1070519 A1 | 1/2001 |
| EP | 1 070 519 | 1/2001 |
| GB | 638223 | 6/1950 |
| GB | 1308041 | 2/1973 |
| WO | WO97/22379 | 6/1997 |
| WO | WO 99/26534 | 6/1999 |
| WO | WO 00/61229 | 10/2000 |

OTHER PUBLICATIONS

Brochure: *Brachytherapy Source Calibration*, Standard Imaging, Middleton, Wisconsin, 8 pgs.; not dated.
Web Site print–out: Source Holders information, Standard Imaging, Middleton, Wisconsin, 2 pgs.; copyright 1998.
Web Site print–out: *Brachytherapy Product Directory*, Med–Tec, Inc., Orange City, Iowa, 1 pg.; Mar. 31, 2001.
Brochure: *HDR 1000 Plus—Ionization Chamber*, Standard Imaging, Middleton, Wisconsin, 15 pgs.; Feb. 15, 2000.
Indigo Express Seeding Cartridge, web page, Dec. 1999.
Seed Plan Pro, web page, Oct. 1999.
Seed Vac, web page, Oct. 1999.

*Primary Examiner*—Kevin Shaver
*Assistant Examiner*—Joseph A. Cadugan
(74) *Attorney, Agent, or Firm*—Patterson, Thuente, Skaar & Christensen, P.A.

(57) ABSTRACT

An automated system for loading low dose radioisotope seeds into a plurality of implant needles includes a loading station into which a replaceable cartridge may be positioned. The cartridge is preloaded with a plurality of radioisotope seeds and a plurality of spacers. The cartridge has at least one aperture and preferably the radioisotope seeds and spacers are loaded around the periphery of a rotatable drum within the cartridge. The loading station has a cartridge receiving structure and an automated motion control system. When the cartridge is positioned in the cartridge receiving structure, the automated motion control system preferably drives a pair of stepper motors within the cartridge, one for rotating the rotatable drum and one for sliding a pushrod to selectively eject radioisotope seeds and spacers from the cartridge into each of a plurality of implant needles positioned so as to receive the radioisotopes seeds and spacers within the implant needle. In one embodiment, the implant needles are positioned tip first into the loading station, and once a predetermined arrangement of radioisotope seeds and spacers are loaded into the implant needle, a plug is positioned in the tip of the implant needle. Preferably, the automated system includes a computer processor having a touch screen user interface that is connected to and directs the operation of the automated motion control system to load the plurality of implant needles in accordance with a predetermined dose plan.

34 Claims, 17 Drawing Sheets

U.S. PATENT DOCUMENTS

| | | | |
|---|---|---|---|
| 4,401,108 A | | 8/1983 | Galkin |
| 4,451,254 A | * | 5/1984 | Dinius et al. ................. 604/62 |
| 4,586,490 A | | 5/1986 | Katz |
| 4,627,420 A | | 12/1986 | Katz |
| 4,649,925 A | | 3/1987 | Dow |
| 4,673,813 A | | 6/1987 | Sanchez |
| 4,702,228 A | | 10/1987 | Russell, Jr. et al. |
| 4,759,345 A | | 7/1988 | Mistry |
| 4,763,642 A | | 8/1988 | Horowitz |
| 4,815,449 A | | 3/1989 | Horowitz |
| 4,847,505 A | * | 7/1989 | Suthanthiran .............. 600/7 X |
| 4,851,694 A | | 7/1989 | Rague |
| 4,869,299 A | | 9/1989 | Handke |
| 4,881,937 A | | 11/1989 | Van't Hooft |
| 4,994,028 A | | 2/1991 | Leonard et al. |
| 5,030,194 A | | 7/1991 | Van't Hooft |
| 5,084,001 A | | 1/1992 | Van't Hooft |
| 5,092,834 A | | 3/1992 | Bradshaw |
| 5,103,395 A | | 4/1992 | Spako |
| 5,120,973 A | | 6/1992 | Rohe |
| 5,147,282 A | | 9/1992 | Kan |
| 5,181,514 A | | 1/1993 | Solomon |
| 5,183,455 A | | 2/1993 | Hayman |
| 5,205,289 A | * | 4/1993 | Hardy et al. ................ 600/7 X |
| 5,242,373 A | | 9/1993 | Scott et al. |
| 5,272,349 A | | 12/1993 | Perry |
| 5,282,472 A | | 2/1994 | Companion |
| 5,339,812 A | * | 8/1994 | Hardy et al. ................ 600/7 X |
| 5,361,768 A | | 11/1994 | Webler |
| 5,391,139 A | | 2/1995 | Edmundson |
| 5,415,169 A | | 5/1995 | Siczek |
| 5,460,592 A | | 10/1995 | Langton et al. |
| 5,540,649 A | | 7/1996 | Bonnell |
| 5,552,645 A | | 9/1996 | Weng |
| 5,626,829 A | | 5/1997 | Kourtrouvelis |
| 5,682,892 A | | 11/1997 | Selder |
| 5,695,500 A | | 12/1997 | Taylor |
| 5,713,828 A | | 2/1998 | Coniglione |
| 5,800,333 A | | 9/1998 | Liprie |
| 5,830,219 A | | 11/1998 | Bird |
| 5,833,627 A | | 11/1998 | Schmulewitz |
| 5,834,788 A | | 11/1998 | Fu et al. |
| 5,851,172 A | | 12/1998 | Bueche et al. |
| 5,851,173 A | | 12/1998 | Dugan |
| 5,860,909 A | | 1/1999 | Mich et al. |
| 5,868,757 A | | 2/1999 | Koutrouvelis |
| 5,871,448 A | | 2/1999 | Ellard |
| 5,906,574 A | | 5/1999 | Kan |
| 5,927,351 A | | 7/1999 | Zhu et al. |
| 5,928,130 A | | 7/1999 | Schmidt |
| 5,931,786 A | | 8/1999 | Whitmore |
| 5,938,583 A | | 8/1999 | Grimm |
| 5,957,935 A | | 9/1999 | Brown |
| 5,961,527 A | | 10/1999 | Whitemore |
| 6,007,474 A | | 12/1999 | Rydell |
| 6,010,446 A | | 1/2000 | Grimm |
| 6,036,632 A | | 3/2000 | Whitemore |
| 6,048,300 A | | 4/2000 | Thornton et al. |
| 6,095,975 A | * | 8/2000 | Sillvern ..................... 600/3 X |
| 6,102,844 A | | 8/2000 | Ravins et al. |
| 6,106,455 A | | 9/2000 | Kan |
| 6,113,529 A | | 9/2000 | Shi |
| 6,129,670 A | | 10/2000 | Burdette |
| 6,196,963 B1 | * | 3/2001 | Williams ....................... 600/3 |
| 6,200,255 B1 | * | 3/2001 | Yu ................................ 600/1 |
| 6,213,932 B1 | * | 4/2001 | Schmidt ........................ 600/7 |
| 6,221,003 B1 | * | 4/2001 | Sierocuk et al. ............... 600/7 |
| 6,241,706 B1 | | 6/2001 | Leschinsky et al. |
| 6,245,008 B1 | | 6/2001 | Leschinsky et al. |

* cited by examiner

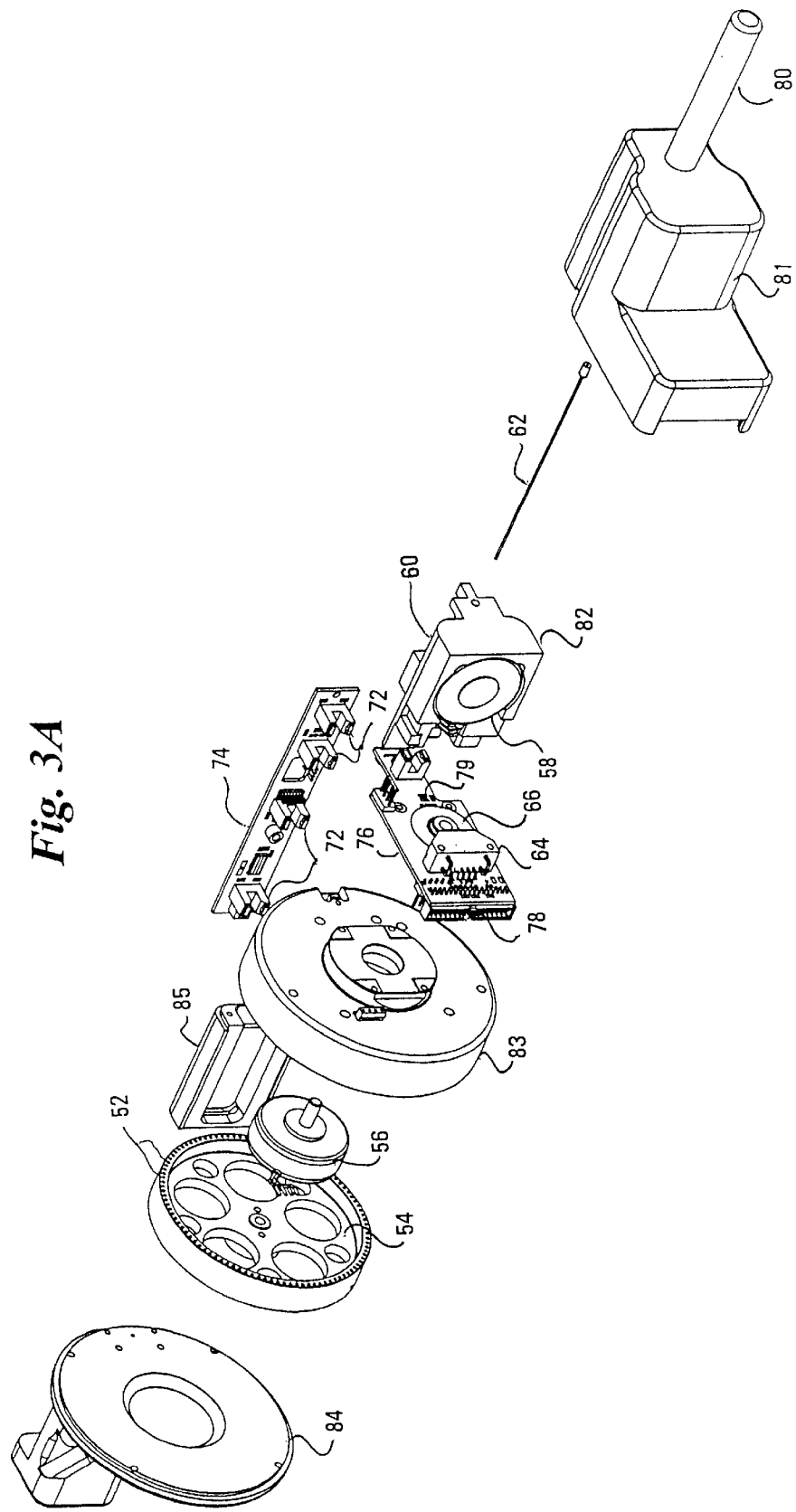

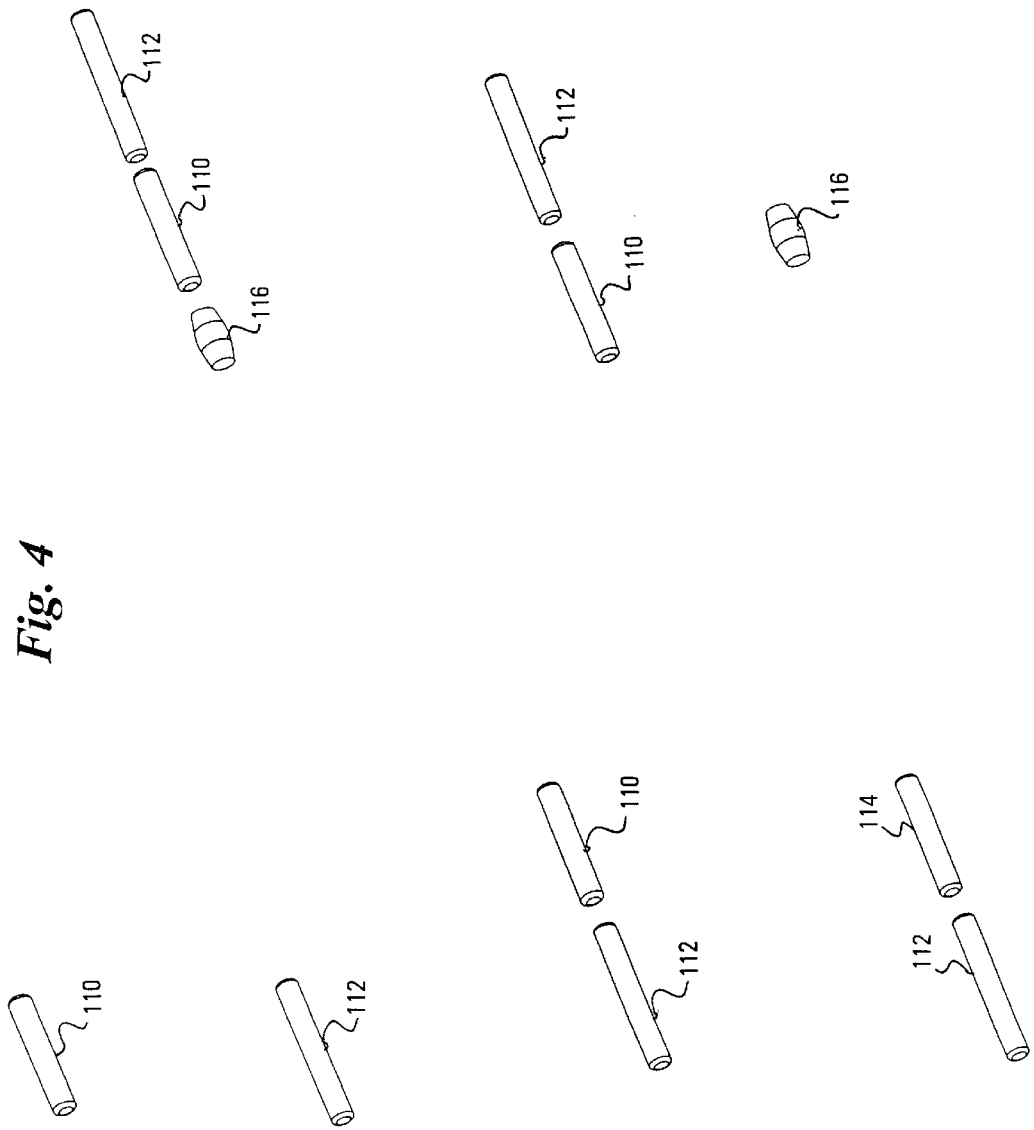

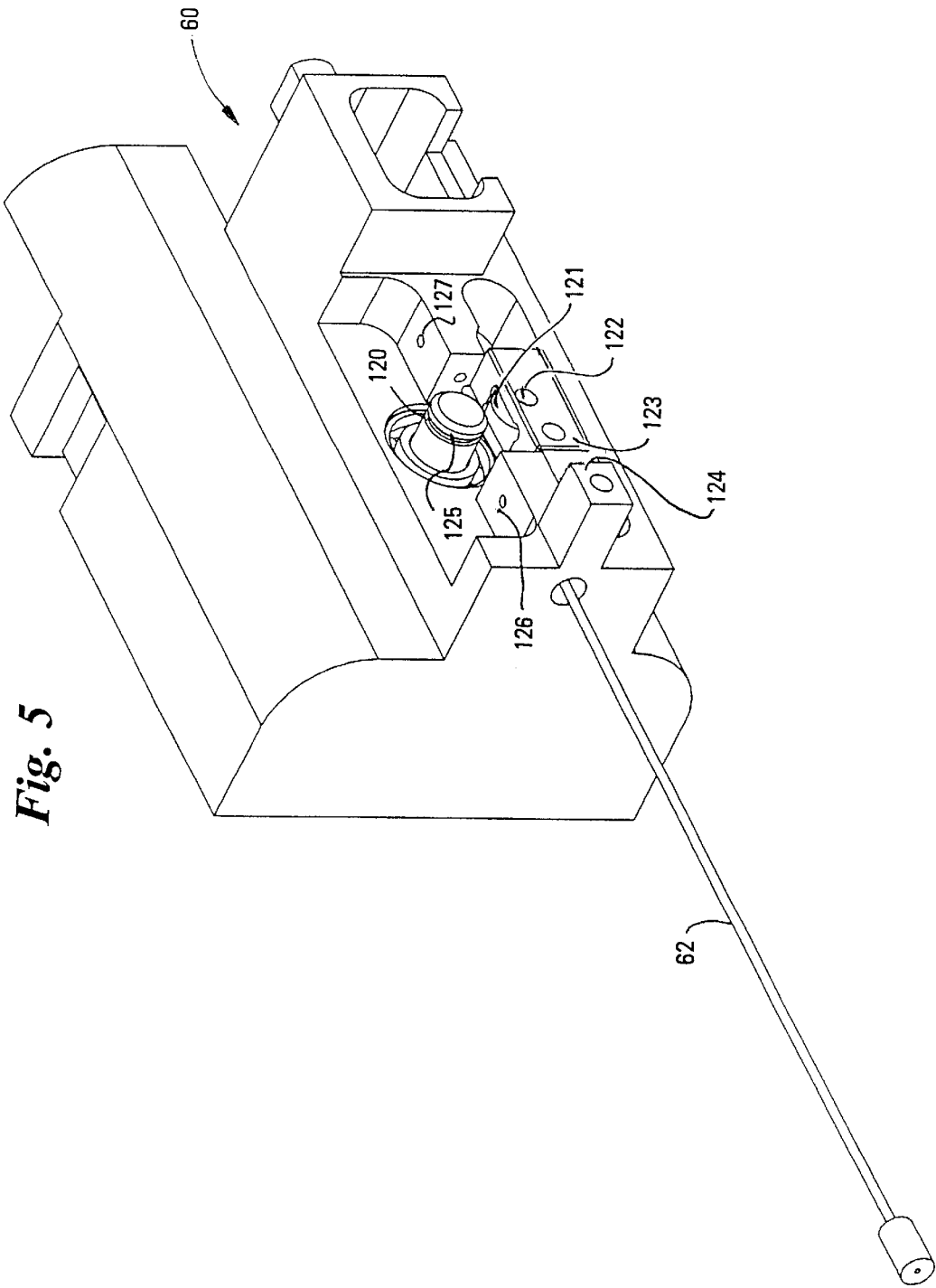

AUTOMATED RADIOISOTOPE SEED LOADER SYSTEM FOR IMPLANT NEEDLES

RELATED APPLICATION

The present invention is related to a co-pending application that is commonly assigned to the assignee of the present invention and filed concurrently herewith, and is entitled "RADIOISOTOPE SEED CARTRIDGE," Ser. No. 09/587,642, a copy of which is attached and the disclosure of which is incorporated by reference.

FIELD OF THE INVENTION

The present invention relates generally to the field of medical devices for handling radioisotope materials. More specifically, the present invention relates to an automated system for loading low dose radioisotope seeds into implant needles for use in brachytherapy procedures or the like.

BACKGROUND OF THE INVENTION

The use of radioisotopes for various medical procedures such as brachytherapy and the like is well known. Such uses fall into two general categories: (i) high dose radioisotopes which are temporarily positioned in relation to a patient's body for a relatively short period of time to effect the radiation treatment, and (ii) low dose radioisotopes which are permanently implanted in a patient's body with the duration of the radiation treatment determined by the strength and half-life of the radioisotope being implanted. High dose radioisotopes are typically implanted using a catheter arrangement and a device commonly known as an afterloader that advances the high dose radioisotope located on the end of a source wire through the catheter to the desired location. Low dose radioisotopes, on the other hand, are implanted using an array of implant needles with the low dose radioisotopes being encapsulated in very small containers known as seeds that are manually loaded into a series of implant needles and then ejected to form a three-dimensional grid of radioisotopes in the patient that corresponds to a dose plan as determined by the physician. The goal of the low dose brachytherapy procedure is to position this three-dimensional grid of radioisotopes seeds in and around a target cancerous tissue area. Each of the radioisotope seeds consists of a radioactive source such as Iodine (I-125) or Palladium (Pd-103) inside a small tube-like titanium shell that is about the size of a grain of rice. These type of low dose radioactive sources emit a very low energy radiation that is primarily absorbed by the tissue immediately surrounding the radioisotope seed. This constant low energy radiation is typically emitted by the radioisotope seeds for a period of up to six months as a way to kill the cancer cells in the target area without having to subject the patient to the discomfort and risks that often accompany high dose radioisotope procedures.

One common brachytherapy procedure is the use of low dose radioisotopes to treat prostate cancer. Although brachytherapy procedures using low dose radioisotopes can be applied to many different parts of the body, it is helpful to describe a particular treatment to gain a better understanding of these treatments. In a typical prostate cancer procedure, a predetermined number of seeds (between 1–6) are positioned within each of a series of implant needles (up to 40), with the seeds being spaced apart in each needle by small spacers. A small amount of bone wax is positioned on the tip of the implant needles to prevent the seeds and spacers from falling out until they are implanted in the patient. The loaded implant needles are then positioned at the appropriate location for insertion into the perineal area of the patient using a stand that has an X-Y coordinate grid. Each needle is manually positioned in the appropriate chamber in the grid and is inserted into the patient. An ultrasound probe is used to assist the physician in guiding each of the needles to the desired location. The seeds and spacers are delivered from the tip of the implant needle using a stylet and hollow needle arrangement where the hollow needle is preferably retracted while the stylet remains in place. When completed, the implanted seeds form a three-dimensional grid of radioisotope sources that implements a predetermined dose plan for treating the prostate cancer in the patient. For a more detailed background of the procedures and equipment used in this type of prostate cancer treatment, reference is made to U.S. Pat. No. 4,167,179.

Over the years there have been numerous advancements in the design of equipment for use in radioisotope procedures. U.S. Pat. Nos. 4,086,914, 5,242,373 and 5,860,909, as well as PCT Publ. No. WO 97/22379, describe manual seed injector arrangements for a low dose radioisotope procedure that utilize drop-in seed cartridges or seed magazines to supply the seeds directly to an implant needle that is specifically adapted to such cartridges or magazines. Similarly, U.S. Pat. Nos. 4,150,298, 5,147,282, 5,851,172 and 6,048,300 describe replaceable cartridge assemblies that contain the source wire used in conjunction with specifically adapted afterloaders that advance the source wire into a catheter systems for high dose radioisotope procedures.

Although such replaceable cartridges have been well received for use in connection with high dose radioisotope procedures, the standard techniques for low dose radioisotope procedures continue to utilize a series of preloaded implant needles that are manually loaded by a radiophysicist at the hospital just prior to the procedure. There are several reasons for why manual loading of the implant needles just prior to use in low dose radioisotope procedures is preferred. First, there are differences in the types of radioisotope sources that do not favor use of a cartridge arrangement for low dose radioisotope procedures. The source wires used for high dose radioisotope procedures use only one or a small number of very high power radioisotope sources having relatively long half-lives. As a result, it is cost effective and practical to provide for a cartridge arrangement for such a small number of high dose radioisotopes that can be preordered and maintained at the hospital well in advance of a procedure. In contrast, given the relatively short half-lives of the radioisotopes used in low dose radioisotope procedures it is preferable that the radioisotope seeds be sent to the hospitals just prior to their use. Because the number of radioisotope seeds varies from procedure to procedure depending upon the dose plan and because the cost of each low dose radioisotope seed is significant, it is not cost effective to order many more radioisotope seeds than will be used in a given procedure. Second, it is important to minimize the time of the procedure, both in terms of the exposure time of the physician to the low dose radioisotope seeds and in terms of the total time of the procedure from the economics of medical practice. The existing drop-in cartridge and seed magazine systems described above take longer to perform the implant procedure than using conventional preloaded implant needles because the radioisotope seeds are implanted one-by-one, rather than being delivered simultaneously as a group from a preloaded needle. Third, it has been routine to employ a radiophysicist at the hospital to preload the implant needles and take a set of sample measurements of the strength of the radioisotope seeds to confirm that the seeds meet the requirements specified by the dose plan. Finally, due to the large number of low dose radioisotope seeds used in a given procedure (typically up to 150) and the need for the implanting physician to be able to modify the dose plan at the time of implant, it is generally considered that the flexibility afforded by manually loading the implant needles just prior to the operation provides the best possible treatment procedure for the patient and the most economically efficient procedure for the hospital.

Although manual preloading of implant needles at the hospital continues to be the norm for most low dose radioisotope procedures, relatively little attention has been paid to increasing the safety or efficiency of this process. Presently, the radioisotope seeds for a given dose plan are shipped in bulk in a protective container to the hospital. At the hospital, the radioisotope seeds are dumped from the container onto a tray where the radiophysicist manually loads the seeds one-by-one into a set of implant needles according to the dose plan. Typically, the implant needles are positioned tip into a needle stand with the tips sealed with bone wax. The radiophysicist picks up a single radioisotope seed using a tweezers, forceps or vacuum hose and deposits that seed in a needle. Next, a single spacer made of gut or similar absorbable material is deposited in the needle. This process is repeated depending upon the predetermined number of seeds and spacers prescribed by the dose plan. The radiophysicist will use a well chamber to measure the strength of a sample of the radioisotope seeds (typically from only one seed to a sample of about 10%). While some needle stands are provided with a certain degree of shielding once the radioisotope seeds are loaded in the implant needles, there is very little shielding that protects the hands and fingers of the radiophysicist during the process of manually loading the implant needles.

U.S. Pat. No. 4,759,345 describes a radiation shielded seed loader for hand implanted hypodermic needles that uses a shielded cylindrical container to house up to seven implant needles. The implant needles have their tips sealed with bone wax and are placed into chambers in an alignment disc. A seed loading disc is located above the ends of the needles and is oriented with each of seven funnels located above a respective end of the needle. The loading procedure occurs behind an L-shaped shielding block and requires the use of a forcep to pick up seeds one at a time and drop them into one of the funnels to be guided into the end of the respective needle. Once each of the needles has been loaded through the funnels in the seed loading disc, the seed loading disc is removed and a plunger is inserted into each needle. Finally, a spacer key distances a cover plate from the ends of the plungers to prevent the plungers from accidentally discharging the seeds during transport. With the cover plate in place, the entire cylindrical container is ready to be transported. Although this type of seed loader would allow for the remote loading of implant needles to be transported in a preloaded fashion to the hospital, if the seeds fall out of the implant needles during shipping or removal of the needles from the container, it is difficult to locate and reload the seeds. The fact that different physicians prefer different types of implant needles further complicates the desirability of using this type of preloaded container.

U.S. Pat. No. 5,906,574 describes a vacuum-assisted apparatus for handling and loading radioisotope seeds within a visible radiation shield. A shielded container with a lead glass window has a vacuum probe that can manipulate and pick up individual seeds. The outlet of the vacuum probe is connected to a lead glass tube such that the operator can verify that the correct sequence of seeds and spacers has been arranged in the lead glass tube. Once the correct sequence has been visually verified, the tip of an implant needle is positioned in a slip shield body and docked on the other end of the lead glass tube. A vacuum force is applied to the back end of the implant needle to suck the seeds and spacers into the implant needle. The implant needle is then undocked from the glass tube and bone wax is used to seal the tip. Once the tip is sealed, the vacuum source is removed from the rear end of the needle and a stylet or plunger is inserted into the needle. The loaded needles with the protective slip shield are placed in a needle holder box until they are to be implanted. While this apparatus improves upon the shielding and safety of the manual process of preloading implant needles, it does not offer any significant improvements to the efficiency of the process.

The same company which provides the vacuum-assisted apparatus for handling and loading radioisotope seeds described in U.S. Pat. No. 5,906,574, also provides several other manual and simple mechanical devices that can be used as part of a manual needle loading process, including a brachytherapy well chamber for taking radiation measurements, an Indigo™ express seeding cartridge for use with the well chamber, a Rapid Strand™ seed carrier as described in U.S. Pat. Nos. 4,815,449 and 4,763,642 which prepositions and encases a series of seeds in a body absorbable material, a seed sterilization and sorting tray, a seed alignment tray, a seed sterilization box, a seed slider for loading needle, and various needle cradles and holders. The Indigo™ express seeding cartridge which is a tube with seeds prepositioned in the tube is only used to accurately index and position individual seeds in the well chamber of a radiation detector for purposes of calibrating the radioisotope seeds. The seed slider interfaces with the seed sterilization and sorting tray that has a seed reservoir for receiving batches of seeds in different wells and sorting area and loading platform. A user scoops seeds from the wells onto the loading platform with the provided spatula. The user then align the seeds and spacers into a slot per treatment prescription. A cover then flips up to encapsulate the seeds and spacers. The needles to be loaded are locked onto one side of the seed slider with a Luer lock. A needle stylet is inserted into the other side of the seed slider and the seeds and spacers are pushed into the treatment needle.

Despite these improvements, the manual loading of implant needles for low dose radioisotope procedures remains a cumbersome process that can expose radiophysicists and other hospital personal to unshielded radioisotopes. It would be advantageous to provide for a system for loading implant needles for low dose radioisotope procedures that could overcome these problems and enhance the safety and efficiency of this process.

SUMMARY OF THE INVENTION

The present invention is an automated system for loading low dose radioisotope seeds into a plurality of implant needles. The automated system is comprised of a loading station into which a replaceable cartridge may be positioned. The cartridge contains a plurality of radioisotope seeds and a plurality of spacers preloaded into the cartridge. The cartridge has at least one aperture and preferably the radioisotope seeds and spacers are loaded around the periphery of a rotatable drum within the cartridge. The loading station has a cartridge receiving structure and an automated motion control system. When the cartridge is positioned in the cartridge receiving structure, the automated motion control system preferably drives a pair of stepper motors within the cartridge, one for rotating the rotatable drum and one for sliding a pushrod to selectively eject radioisotope seeds and spacers from the cartridge into each of a plurality of implant needles. In one embodiment, the implant needles are positioned rear first into the loading station. In another embodiment, the implant needles are positioned tip first into the loading station. Once a predetermined arrangement of radioisotope seeds and spacers are loaded into the implant needle, a plug is positioned in the tip of the implant needle. Preferably, the automated system includes a computer processor having a touch screen user interface that is connected to and directs the operation of the automated motion control system to load the plurality of implant needles in accordance with a predetermined dose plan.

In a preferred embodiment, the cartridge receiving structure is defined in a front side of the loading station oriented toward a user. Several features of the preferred embodiment improve the ease of operation and minimize the potential for misalignment within the automated system. The cartridge receiving structure defines a downwardly angled path of travel for inserting the cartridge into the cartridge receiving structure. The interface between the cartridge and the cartridge receiving structure is primarily an electrical connection in the preferred embodiment as the stepper motors and associated encoder discs are contained within the cartridge, thereby minimizing the need for extremely tight tolerance matches between the cartridge receiving structure and the cartridge. Once in position, the loading station locks the cartridge in place using an electrical solenoid to prevent inadvertent removal.

Preferably, the cartridge includes a machine readable storage medium, such as an EEPROM, that stores indicia representing at least the quantity and location of the radioisotope seeds preloaded in the cartridge. The computer processor in the automated system is preferably provided with a machine readable format of the predetermined dose plan. The computer processor is programmed to use the information in the EEPROM and the predetermined dose plan in a dynamic fashion so as to cause the automated motion control system to selectably position the rotatable drum in the cartridge relative to the aperture and eject the proper number of radioisotope seeds and spacers into each needle in accordance with a predetermined dose plan. Optionally, a user can interact with the user interface of the computer system to alter the predetermined dose plan during the process of loading the implant needles if necessary. Preferably, the touch screen interface displays a graphic representation of the coordinates of each needle to be loaded, with the user selecting the next needle to be loaded by touching one of the coordinates. As the coordinate is touched, the icon associate with that coordinate would change color indicating that that needle had been loaded. In addition, as each needle is loaded, a graphic representation of a cross-section of the needle is displayed to allow a user to confirm visually the proper loading of radioisotope seeds and spacers within the implant needle.

In a preferred embodiment, a position sensor along the path of the push rod is used to detect and register the position of the tip of the pushrod to monitor and confirm the proper loading of radioisotope seeds and spacers in to the implant needle. Further confirmation of the proper loading of the radioisotope seeds can be accomplished by a radiation sensor that detects a radiation level of the radioisotope seeds after they are ejected from the cartridge. Unlike existing systems which make only sample measurements of radiation levels, the present invention can confirm the properly radiation level of each radioisotope seed. Alternatively, a user may select to monitor the radiation level of only the first radioisotope seed ejected into an implant needle or only a given number of the radioisotope seeds.

As a further enhancement of the flexibility of the present invention, different sized spacers may be utilized with the present invention. In one embodiment, spacers loaded into the cartridge may be either a full-length spacer or a smaller-length spacer, where the full-length spacer has a length slightly longer than the length of a radioisotope seed. The use of a smaller-length spacer is advantageous in certain circumstances where it is desirable to offset the spacing of the radioisotope seeds in adjacent planes of the predetermined dose plan. Presently, the only way to accomplish this is by having the radio physicist manually cut a portion from a full-length spacer prior to loading it into an implant needle. Typically, a radioisotope seed for a prostate cancer procedure will have a length of 4.5 mm, with a full-length spacer having a length of approximately 5.5 mm. Although this embodiment is preferably contemplated in terms of using full-length and half-length spacers, the present invention affords the ability to customize the length of the smaller-length spacers as desired. In another embodiment, a special size spacer referred to as a blank is provided that has a length equal to the length of a radioisotope seed. Blanks are used to maintain spacing of adjacent planes in a dose plan by allowing a given location that should contain a seed in a typical seed—spacer—seed —spacer arrangement to contain a blank in the place of a seed without altering the longitudinal spacing of this typical arrangement.

In an alternate embodiment, the stepper motors for driving the rotatable drum and the pushrod are located in the loading station, instead of in the replaceable cartridge. In this embodiment, the front side of the loading station includes a pivotable door that operates in a close positioned as a shield when the cartridge is positioned in the cartridge receiving structure and in an open position as a tray for retaining loose radioisotope seeds and spacers. When the cartridge is in position in the cartridge receiving structure, a first drive wheel and a position encoder in the cartridge are operably engaged by a second drive wheel and a position sensor in the loading station to drive and sense the position of the rotatable drum in the cartridge. A position registration mechanism preferably positions the cartridge within the cartridge receiving structure within the tolerance of +/−0.010 inches. Preferably, the position registration mechanism comprises a ball and detent mechanism with cartridge having at least one detent defined on our surface and a loading station having a cam driven ball mechanism that selectively seats at least one ball in the least one detent to properly register the position of the cartridge within the cartridge receiving structure. The loading station also includes at least one guide rail having a push rod connected to a linear actuator that is controlled by the automated motion control system to selectively eject the radioisotope seeds and spacers from the periphery of the rotatable drum of the cartridge.

The automated system of the present invention advantageously uses a replaceable cartridge to transport and dispense the radioisotope seeds in a manner much safer and more efficient than current conventional manual practices. The replaceable cartridge. is provided with sufficient shielding to insure safe handling of the low dose radioisotope seeds. The positioning of the radioisotope seeds around the periphery of a rotatable drum within the replaceable cartridge further serves to minimize safety issues by preventing a buildup of radioisotope seeds at any one location within the cartridge.

BRIEF DESCRIPTION OF THE DRAWINGS

FIGS. 3A and 3B are exploded perspective views of the preferred embodiment of the replaceable cartridge of FIG. 1 that loads needles from the rear.

FIG. 4 is a schematic representation of the various combinations of radioisotope seeds, spacers and plugs as stored in the rotatable drum of the preferred embodiment of the replaceable cartridge of FIG. 3.

FIG. 5 is a detailed view of a capstan assembly for the push rod of the preferred embodiment of the replaceable cartridge of FIG. 3.

DETAILED DESCRIPTION OF THE PREFERRED EMBODIMENT

Figure 1A:
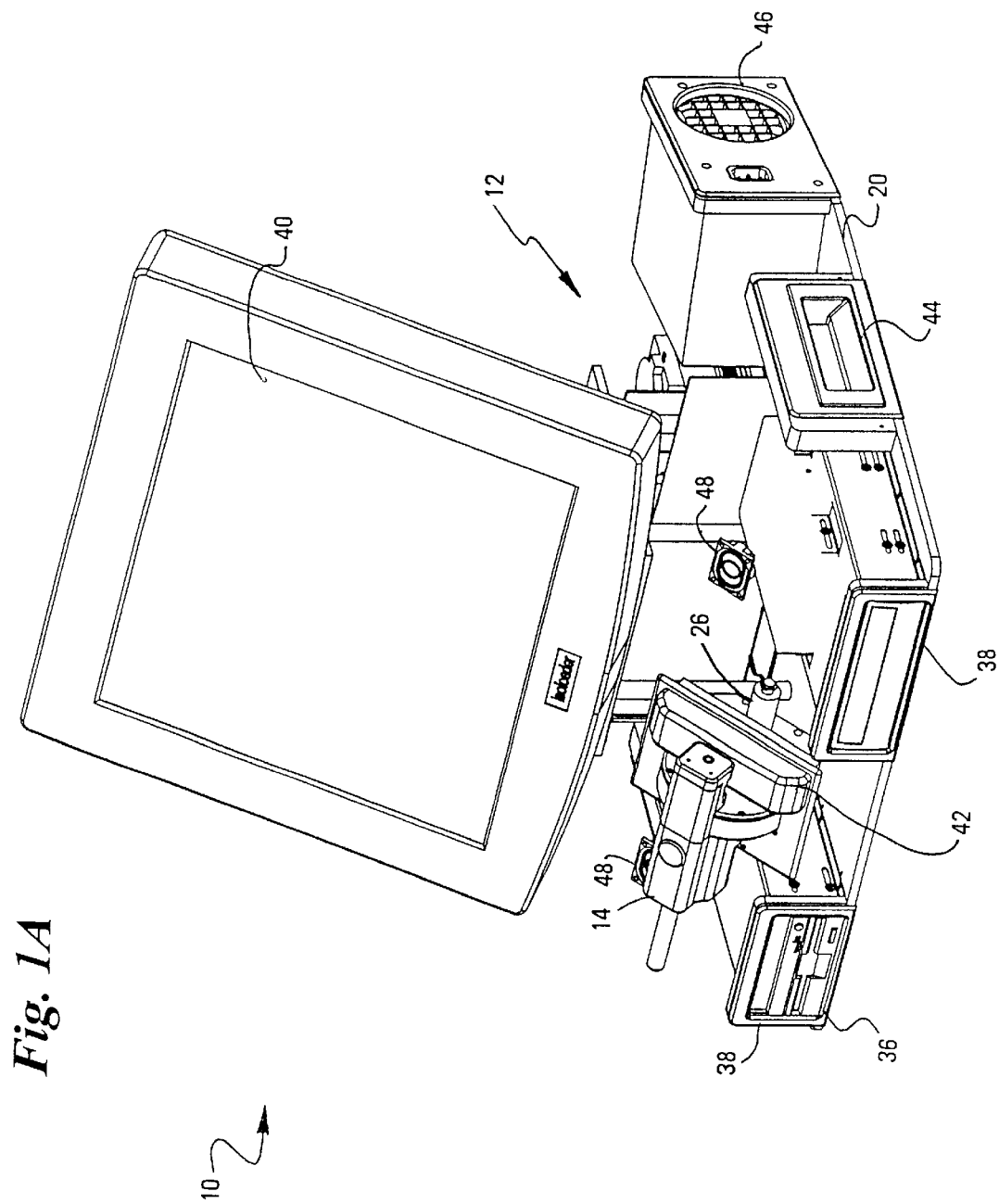
FIGS. 1A and 1B are perspective views of a preferred embodiment of the automated system for loading low dose radioisotope seeds and showing the preferred embodiment of the replaceable cartridge of the present invention in place within the automated loading system.
Figure 1B:
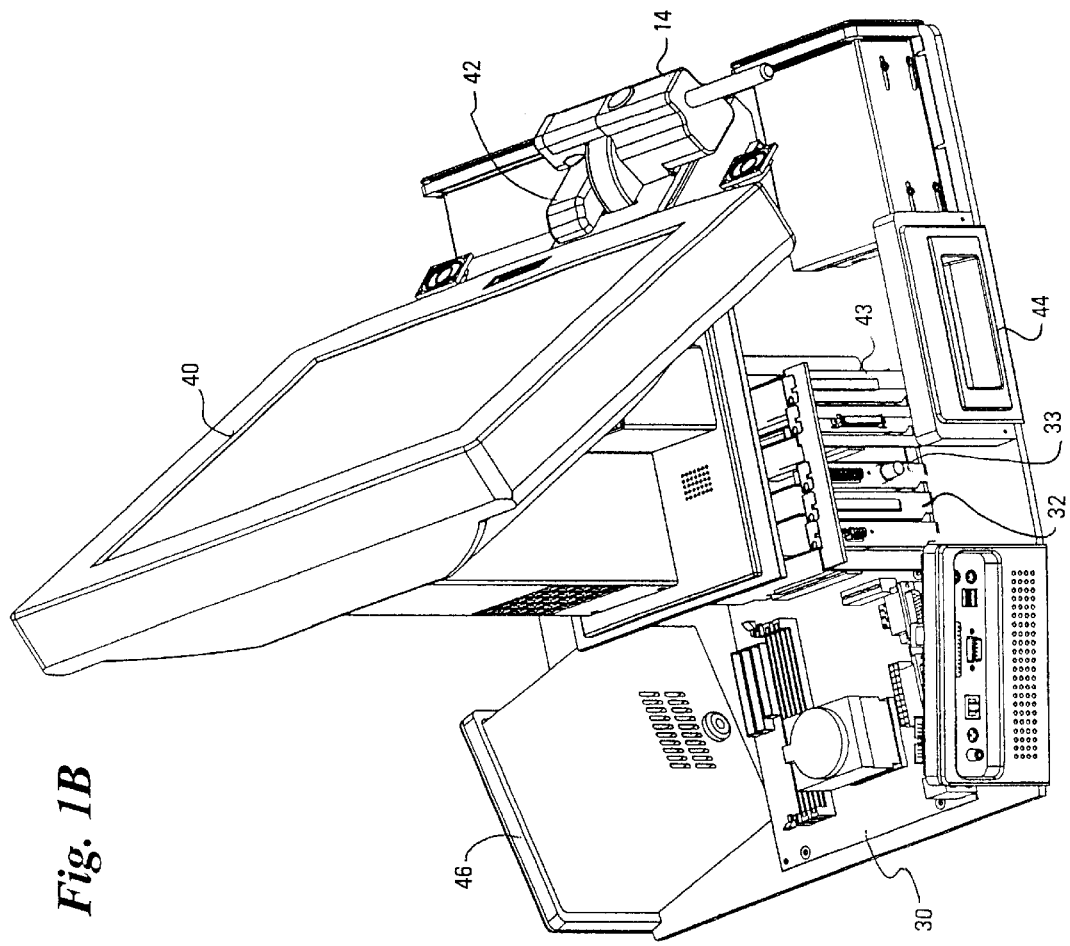
Figure 2:
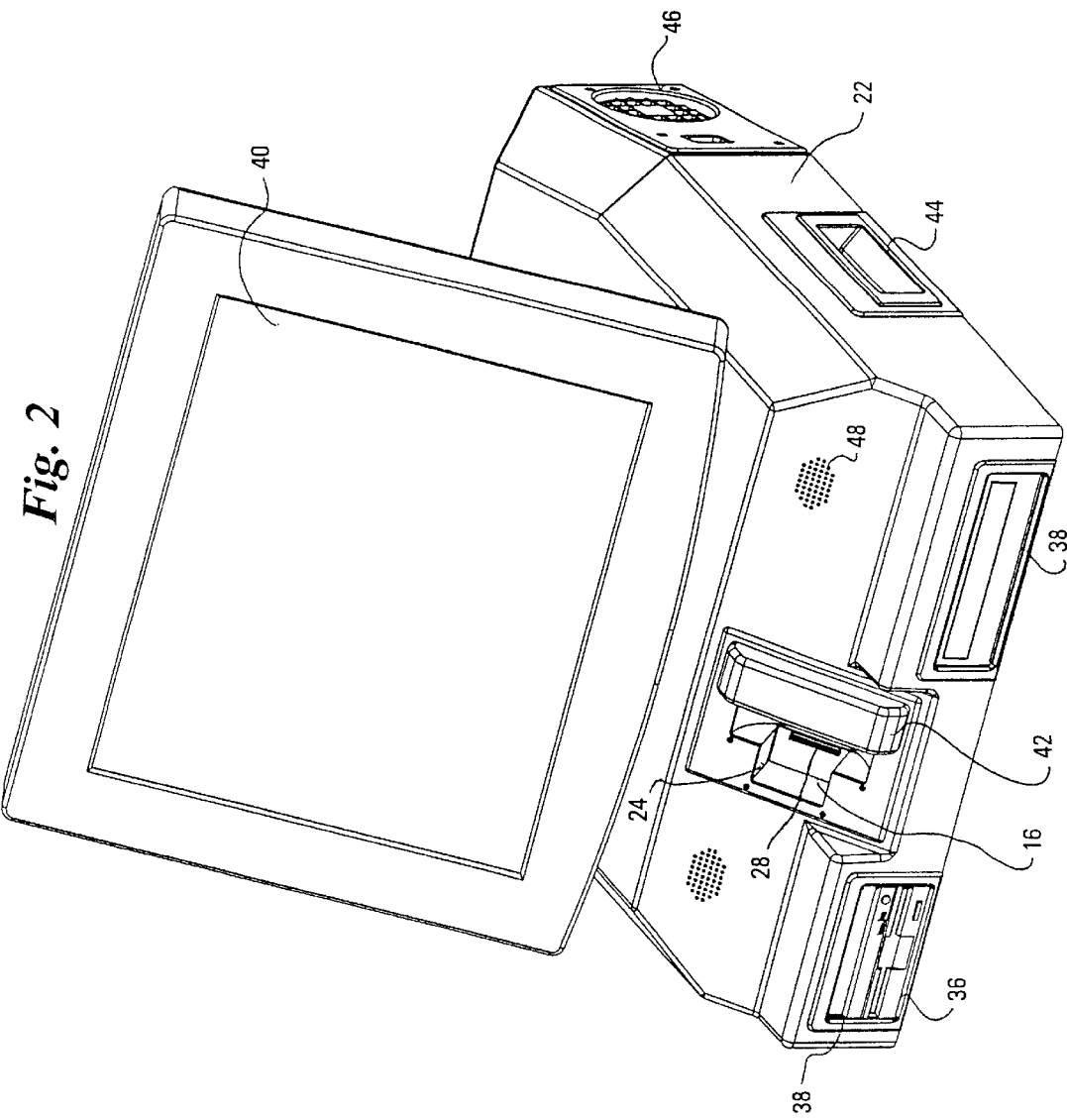
FIG. 2 is a perspective of the automated system of FIG. 1 with an enclosure and showing the receiving structure that mates with the replaceable cartridge of the preferred embodiment of the present invention.

Referring to FIG. 1, an automated system 10 for loading low dose radioisotope seeds into a plurality of implant needles is comprised of a loading station 12 into which a replaceable cartridge 14 may be positioned. Preferably, the loading station 12 includes structure defining a cartridge receiving structure 16 in a front side of the loading station oriented toward a user as shown in FIG. 2. In this embodiment, the loading station 12 presents a front side toward a user with a corresponding longer dimension of the replaceable cartridge positioned in the cartridge receiving structure 16 parallel to this front side. Alternatively, the cartridge 14 and cartridge receiving structure 16 could be oriented transverse to the front side of loading station 12 or even at a rear side of loading station 12.

The loading station 12 has a base 20 (as shown in FIG. 1) and a cover 22 (as shown in FIG. 2) preferably formed of molded plastic or metal. A computer processor 30 for the automated system is preferably a motherboard having a microprocessor, internal bus, a PCI-compatible bus, DRAM and EPROM or battery backed SRAM, with appropriate external interfaces or mated PC boards for a video interface, multiple channel IDE interfaces, a floppy disk interface, an ethernet interface, COM and LPT interfaces, an external bidirectional parallel port and a serial port. An automated motion control system 32 is preferably a Galil motion controller available from Galil Motion Control Inc. that interfaces to the computer processor 30 via the PCI-compatible bus. The automated motion control system 32 with appropriate software drivers provides all functionality for the lowest level control of stepper motor position and feedback sensors. A hard disc drive 34, floppy disk drive 36, high density removable media drive 37 and CD or CD-RW drive 38 are also provided for storing data and information to be used by the automated system 10. A video display 40 which operates as the primary user interface is preferably a 1280 by 1024 resolution flat 18.1 inch flat panel LCD with a resistive touch screen, such as are available from National Display Systems. Alternatively, a conventional non-touch screen video display and mouse, keyboard or similar input devices could also be provided. A proportional counter type radiation sensor 42 is positioned to be able to sense the passage of radioisotope seeds from the cartridge 14 into the implant needles and verify the radiation strength of the radioisotope seeds. In the preferred embodiment, the radiation sensor 42 is connected to a multi-channel analyzer card 43 that serves as a data acquisition device for information from this sensor. For clarity, none of the interconnections or cables among the various elements are shown in FIG. 1. FIG. 2 shows one of a pair of handles 44 for carrying the loading station 12 and one of two fan units 46 for cooling the circuitry and components of the loading station 12. Speakers 48 are also included in the front of the loading station 12.

Referring specifically to FIG. 2, the downwardly angled cartridge receiving structure 16 of the preferred embodiment will be described. The cartridge receiving structure 16 includes an angled channel 24 with sides that define a downwardly angled path of travel for inserting at a preferred angle of approximately 45 degrees. Once in position, the loading station 12 locks the cartridge in place using an electrical solenoid 26 to prevent inadvertent removal of the cartridge 14 during operation of the automated system 10. Locking is initiated automatically once the presence of a cartridge 14 has been detected in the cartridge receiving structure 16 and the user has initiated a loading operation via display 40. Unlocking the cartridge is initiated by the user selecting a remove cartridge operation via display 40, but only after computer processor 30 has confirmed completion of any critical motions that are part of the needle loading operation and removed power to the cartridge 14. Preferably, the only other interface between the cartridge 14 and the cartridge receiving structure 16 is a multiple pin-type electrical connector 28. As the stepper motors and associated encoder discs are contained within the cartridge 14, the need for extremely tight tolerance matches between the channel 24 of the cartridge receiving structure 16 and the cartridge 14 is minimized. In addition to the necessary control and sensor signals, the connector 28 include a ground and power connection to provide power to the cartridge 14. The presence of cartridge 14 in cartridge receiving structure 16 is also detected via a contact on connector 28. Although an angled channel 24 is the preferred embodiment for interfacing the cartridge 14 with the cartridge receiving structure 16, it will be recognized that many other structures, such as guide rails, latches, pivoting arrangements, ball and detent locks, and orientations, such as horizontal or vertical, and connectors, such as optical, infrared, RF, slide contacts, array contacts or the like, could be used to accomplish the same function of interfacing the cartridge 14 with the cartridge receiving structure 16.

Figure 3B:
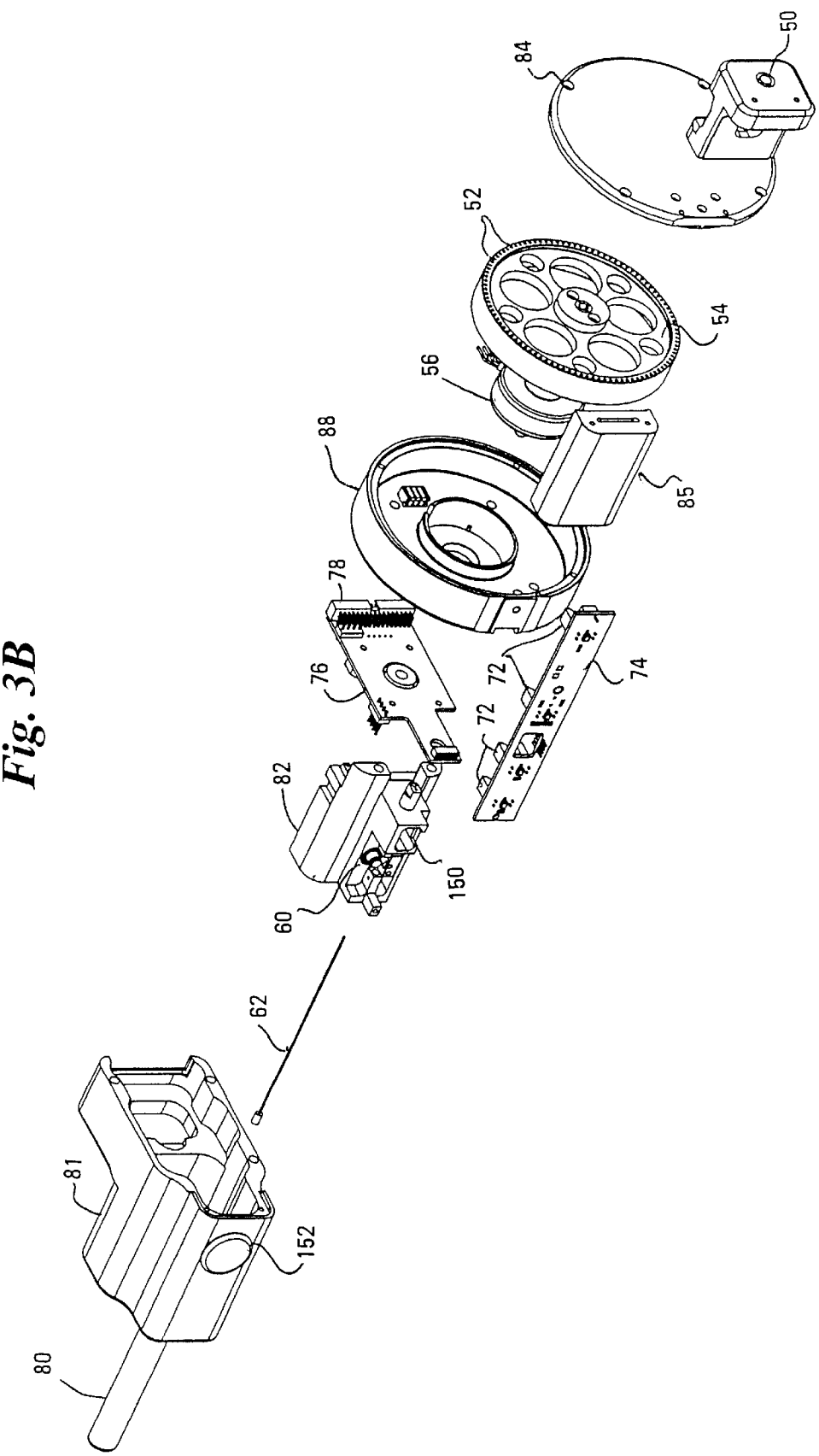

Referring now to FIGS. 3A and 3B, the cartridge 14 contains a plurality of radioisotope seeds and a plurality of spacers preloaded into the cartridge. The cartridge 14 has at least one aperture 50 into which an implant needle is positioned. Preferably, the radioisotope seeds and spacers are loaded into holes or chambers 52 located around the periphery of a rotatable drum 54. In this embodiment, the cartridge 14 includes a pair of stepper motors within the cartridge. A first stepper motor 56 rotates the rotatable drum 54. It will be seen that stepper motor 56 preferably drives rotatable drum 54 directly without any intervening gearing arrangement. A second stepper motor 58 has a capstan assembly 60 that rotates in engagement with a push rod 62 to slide the push rod 62. For the rotatable drum 54, an encoder detector 64 detects the position of a corresponding encoder disc 66 which is then communicated back to automated motion control system 32 (FIG. 1). Preferably, the stepper motor and encoder are selected such that the stepper motor steps in full steps with relation to the distance between chambers around the periphery. The alignment of the aperture to the chambers in the drum is preferably initially accomplished at the time of assembly. It will also be seen that other motor drives other than stepper motors could be used with equivalent success in the present invention, such as servo motors, worm driven motors, or DC motors with appropriate indexing control.

Figure 7:
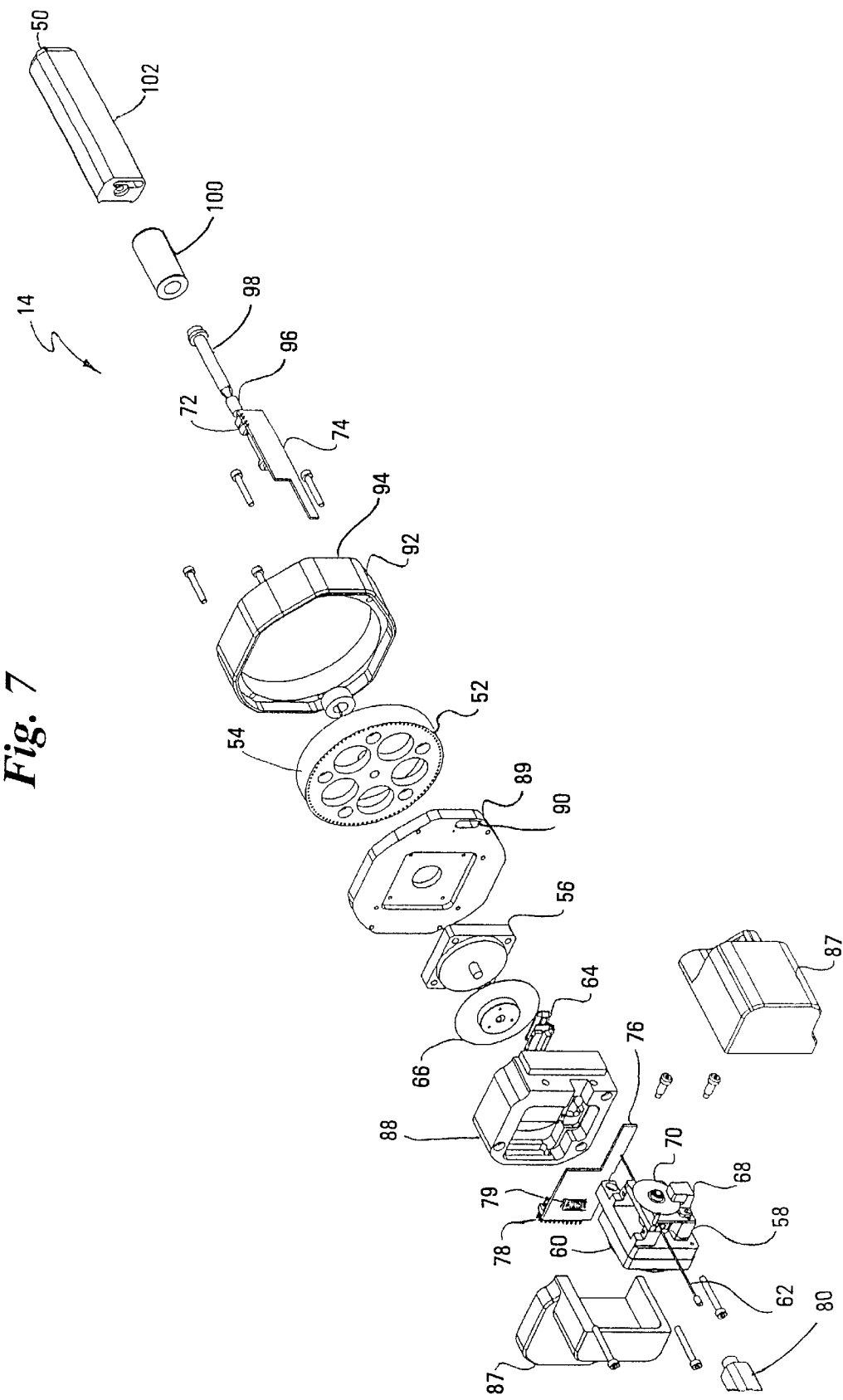
FIG. 7 is an exploded perspective view of an alternative embodiment of the replaceable cartridge that loads needles from the tip.

In an alternative embodiment as shown in FIG. 7, an encoder with a higher degree of resolution can be used and the stepper motor can be incremented in less than full steps. In this embodiment, a first encoder for the rotatable drum generates a positional feedback signal of an index of the chambers of the rotatable drum relative to the line of travel of the linear actuator 60, and a second encoder 68 with a second encoder disc 70 for the linear actuator 60 that generates a positional feedback signal of a position of the elongated member along the line of travel.

Referring again to FIG. 3, a series of position sensors 72 are positioned in line with the push rod 62 to detect the travel of push rod 62 as it is driven by capstan system 60 through its line of travel. The sensors 72 are connected to sensor circuitry 74 to communicate this position information to the automated motion control system 32. Each of the encoder detector 64 and sensor circuitry 74 are electrically connected to a circuit board 76 which has an appropriate connector 78 for mating with and connecting with a corresponding connector 28 (FIG. 2) in the cartridge receiving structure 16 of the housing 12.

Preferably, the circuit board 76 is provided with an electrically eraseable programmable read-only memory (EEPROM) 79 or similar non-volatile memory to store parameters and other data that are unique to the particular cartridge 14 and to the particular patient and dose plan that has been developed for that patient. The contents of EEPROM 79 are set up initially during loading and calibration of the cartridge 14 at the factory. These contents are updated by the automated system 10 so as to continually reflect the current state of the cartridge 14. For example, when the radioisotope seeds and/or spacers are ejected from a given chamber 52, then the data on the EEPROM 104 is updated to reflect that the given chamber 52 no longer contains any radioisotope seeds and/or spacers. Preferably, the EEPROM 79 is capable of storing patient and hospital identification information, as well as seed inventory and manufacture information. Optionally, the EEPROM could also store the predetermined dose plan for the particular patient.

In the preferred embodiment, various housing elements enclose the cartridge 14 to create a single, enclosed drop-in cartridge to simplify operation and handling of the cartridge as shown in FIG. 3. Preferably, the various housing elements are formed of machined stainless steel to enhance the protective aspect of the housing. Alternatively, the housing could be formed of materials other than stainless steel. For example, the housing elements could be molded plastic with appropriate pieces having an internal lead lining or the like to provide sufficient shielding. Although the preferred embodiment is described as a single, enclosed drop-in cartridge, it will be understood by those skilled in the art that some or all of the functional components of cartridge 14 may be separately enclosed or left unenclosed and operably connected together to accomplish the same functionality, such as allowing for mating with the cartridge receiving structure 16 and protecting movement of the push rod 62 along its line of travel.

In the preferred embodiment of the rear loading cartridge 14 as shown in FIG. 3, a push rod sleeve 80 encloses the travel of push rod 62. Cover 81 is a one piece unit that covers the capstan assembly 60 and its associated components. A capstan motor mount 82 provides a mounting base for most of the main components of cartridge 14, including circuit board 76 and encoder detector 64. Housing 83 houses the stepper motor 56 and the rotatable drum 54. A cover plate 84 mounts to the housing plate 83. The motor mount 82 and the cover 81 are secured by internal screws (not shown) that are accessed when the cover plate 84 is removed. A front plate 85 covers the circuit board 74 and is also mounted with screws between cover plate 84 and cover 81. A needle housing 86 is also screwed on to the cover plate 84 and includes the aperture 50 through which the needle accesses the cartridge.

Figure 6:
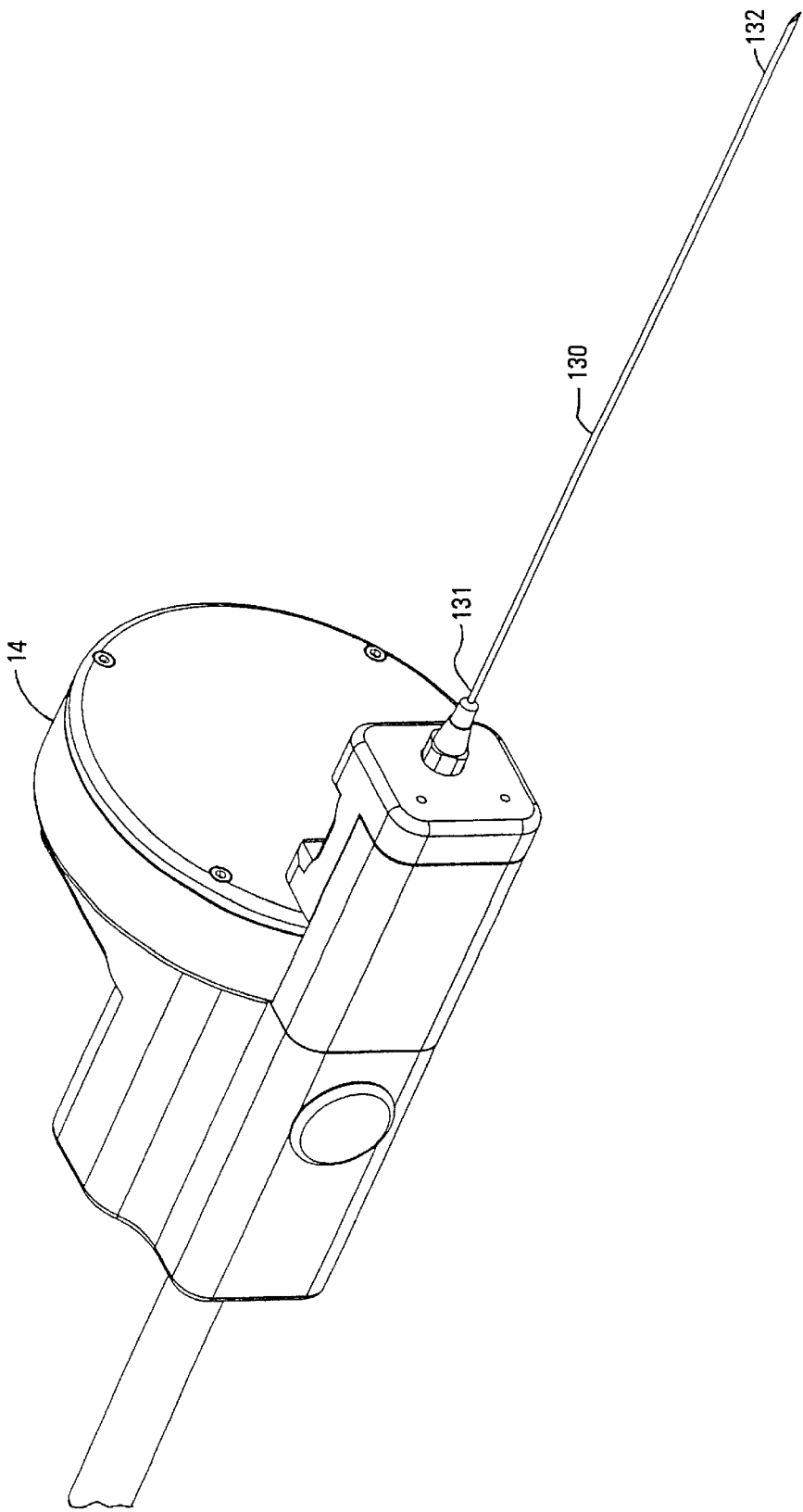
FIG. 6 is a perspective of the assembled replaceable cartridge of FIG. 3 with a needle to be loaded from the rear.

In the preferred embodiment as shown in FIG. 6, the contents are loaded into the rear 131 of the implant needle 130 which has its tip 132 plugged with bone wax or a similar plug material. Alternatively, a crimp at the tip 132 could prevent the contents of chamber from being pushed out the tip 132 of the needle 132 as it is loaded from the rear 131. In this embodiment, the rear 131 of the needle 130 is preferably secured in place in the aperture 50 by a Luer lock or similar assembly. Preferably, the tip 132 does not extend beyond the side of loading station 12 as a safety measure.

Figure 9:
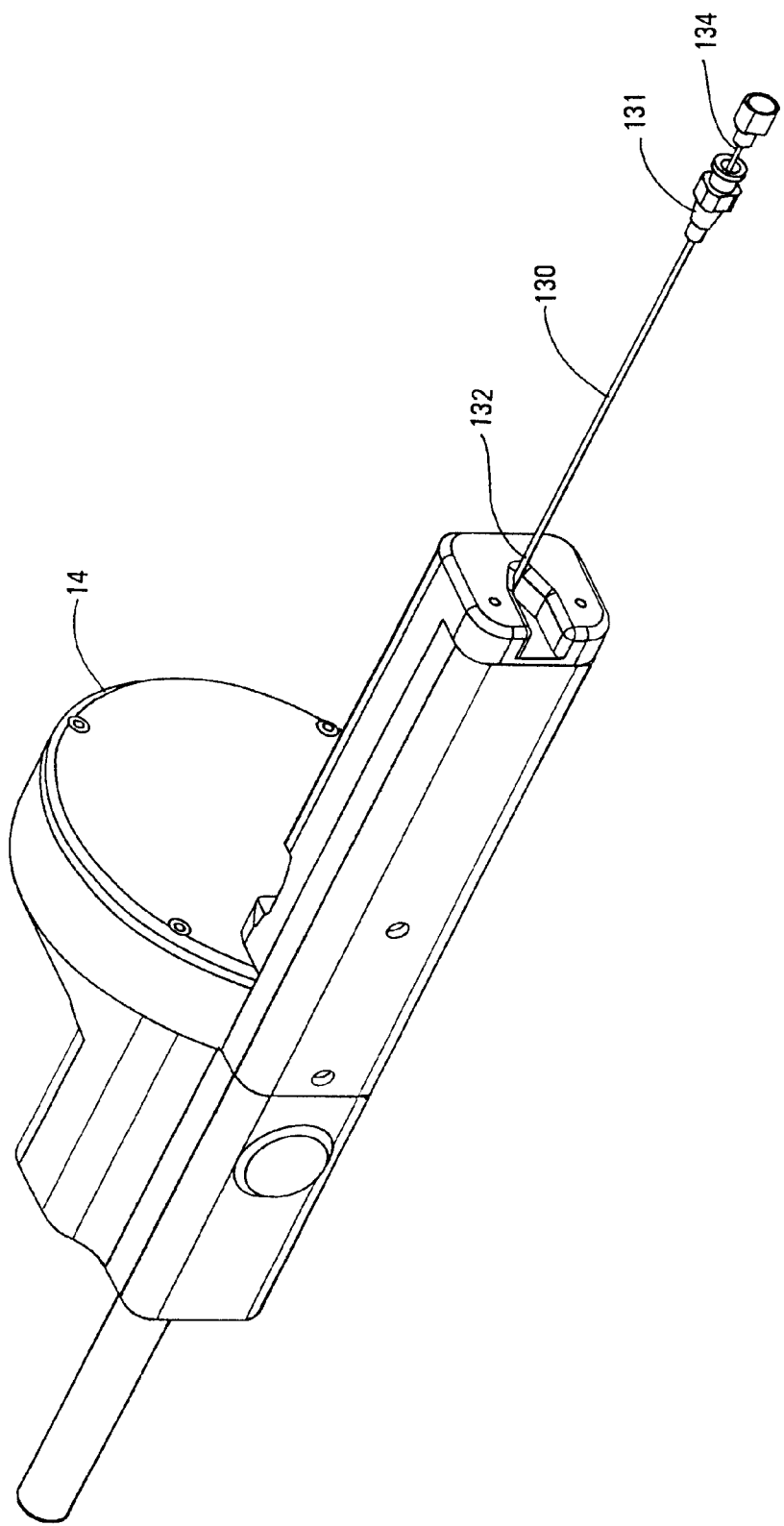
FIG. 9 is a perspective view of an assembled replaceable cartridge with a needle to be loaded from the tip.

In an alternate embodiment as shown in FIGS. 7 and 9, the contents are loaded into the tip 132 of the needle 130, rather than into the rear 131 of the needle 130. In this embodiment, the housing elements are configured somewhat differently than in the rear loading embodiment. A rod sleeve 80 encloses the travel of push rod 62. Housing halves 87 mate to abase 88 to cover the capstan assembly/linear actuator 60 and its associated components. The base 88 provides a mounting base for most of the main components of cartridge 14 of the tip loading embodiment, including circuit board 76 and encoder detector 64. Plate 89 provides a mounting structure for stepper motor 56 and includes an aperture 90 through which push rod 62 slides to engage the radioisotope seeds and spacers located in the chambers 52 around the periphery of rotatable drum 54. Plate 89 also prevents radioisotope seeds and spacers from falling out of the chambers 52 on one side of rotatable drum 54. A cap-like cover 92 is mounted over the other side of rotatable drum 54 and includes an aperture 94 by which access is provided to sensor circuitry 74 and through which push rod 62 slides to eject the radioisotope seeds and spacers into the implant needle (not shown) via an alignment tube 96. An alignment structure 98 preferably comprising a beveled alignment needle guide has an internal channel that aligns a corresponding beveled implant needle with the alignment tube 96. An electrical solenoid 100 is used to lock the implant needle in place relative to the cartridge 14 once the proper positioning of the implant needle in the alignment structure 98 has been confirmed. In the this embodiment, the at least one aperture 50 is defined on an end of a shield tube 102 constructed of appropriate metal to shield the radioisotopes as they are being loaded into the implant needle.

In addition to the advantages afforded by constructing cartridge 14 as a single, enclosed drop-in cartridge, the preferred embodiment of cartridge 14 is designed with minimum piece parts to allow for easy disassembly and sterilization to allow for potential re-use. Once the various covers and circuit assemblies are removed, the remaining portions of cartridge 14 are cleaned with alcohol or hydrogen peroxide to remove bioburden. When reassembled, the entire cartridge 14 is preferably sterilized with a gas sterilization technique. The ease of disassembly also provides a convenient mechanism by which emergency removal of the radioisotope seeds can be accomplished, simply be removing cover 92 and dumping the radioisotope seeds and spacers into an appropriate container.

The use of a rotatable drum 54 also affords important advantages to the preferred embodiment of the present invention. The positioning of the chambers 52 around the periphery of drum 54 reduces the concentration of radiation sources at any given point and provides an optimum separation of radioisotope seeds from each other, thereby enhancing the safety of cartridge 14.

In the preferred embodiment, each chamber 52 is long enough to accommodate any of a combinatorial set of radioisotope seeds, spacers and plugs. As shown in FIG. 4, various combinations of radioisotope seeds 110, full-length spacers 112, partial-length spacers 114 which can serve as blanks and plugs 116 can be positioned within a given chamber 52. In this embodiment, the length of one radioisotope seed 110 or one blank 114 is 4.5 mm, the length of one full length spacer 112 is 5.5 mm and the length of one plug 116 is 2 mm. As will be apparent, the selection of the lengths of each of the seeds 110, spacers 112, 114 and plugs 116 allows for various combinations to be utilized that have the same overall length when positioned in an implant needle of 10 mm for seed and spacer or 12 mm for seed, spacer and plug. The particular combination of each for a given cartridge is optimally determined at the time that the cartridge 14 is preloaded in accordance with a predetermined dose plan. This information can then be utilized by the automated station 10 to load the implant needles in accordance with that predetermined dose plan.

In the preferred embodiment, the rotatable drum 54 is provided with 200 chambers 52 spaced equidistant about the periphery of the rotatable drum 54. The optical encoder disc 66 preferably has 400 or 1600 lines of resolutions which yields a resolution of 2 or 8 counts per chamber 52. In an alternate embodiment with higher resolution as previously described, 72,000 lines of resolution are used which yields a resolution of 360 counts per chamber 52. A home reference is provided by an index channel on the encoder disc 66. The alignment of the aperture 50 to the chambers 52 in the drum 54 using the index channel is preferably accomplished at the time of assembly. In the high resolution embodiment, an offset to a first chamber location clockwise from the home reference is stored as a parameter for the cartridge 14 to allow for individual cartridge tolerance calibration. Alternatively, an optical sensor could be used to locate the center of a chamber 52 for purposes of calibrating an index. In operation, the automated motion control system 32 uses the stepper motor 56 and encoder circuitry 64 to establish a reference to the first seed drum chamber 52. Motion of the drum 54 may take place bidirectionally (i.e., clockwise or counterclockwise) and as rapidly as possible in order to move to the nearest desired chamber location as determined by the computer processor 30 and automated motion control system 32 in the shortest possible time. When requested by the computer processor 30, the automated motion control system 32 will index to the center of the desired chamber location in preparation for transfer of the contents of that chamber 52 to the implant needle. The drum 54 will remain at this location until it is commanded to a new position.

Referring now to FIG. 5, a preferred embodiment of the capstan assembly 60 will be described. A pair of capstans 120, 121 are positioned above and below the line of travel of push rod 62. The upper capstan 120 is preferably the shaft of stepper motor 58. The lower capstan 121 is preferably a ball bearing 122 held in a biased pivot arm 123 biased by a spring 124. Preferably, the upper capstan 120 includes a radial channel 125 adapted to guide the push rod 62. The pivot arm 123 pivots back to allow the push rod 62 to enter the capstan assembly 60. Once engaged, the channel 125 guides the push rod 62 as it is frictionally held between capstans 120, 121. In the preferred embodiment, the channel 125 is aligned with respect to the chambers 52 by adjusting the motor 58 that drives the capstan assembly 60 to the desired depth. A positive travel limit is preferably established using a first optical sensor 126 that is part of the structure of capstan assembly 60 which detects the back of the push rod 62 passing through a defined point. A negative travel limit for the line of travel of push rod 62 is established by a second optical sensor 127 that doubles as a home reference. Preferably, the travel limits do not disable the stepper motor 58, but rather send an indication to the automated motion control system 32 that the respective travel limit has been exceeded. Once zeroed in relation to the home reference, the push rod 62 is moved forward and into an open chamber 52 in the drum 54. This serves as a loose mechanical lock to prevent the drum 54 from being rotated unintentionally. When a request for a seed transfer is generated by the computer processor 30, the automated motion control system 32 activates the capstan assembly 60 to retract the push rod 62, thereby allowing the drum 54 to be rotated freely.

When the drum 54 has been indexed to the desired chamber location, the automated motion control system 32 instructs the stepper motor 58 to move the push rod 62 forward to push the contents of the chamber 52 out of the drum 54 and into the tube 96 leading to the radiation sensor 42. The distance the push rod will travel will be based on the total length of the contents in the given chamber and the location of the radiation sensor 42. Because the automated motion control system 32 knows the nature of the contents of each chamber 52, the push rod would be instructed to stop and position the radioisotope seed in front of the radiation sensor 42 if a radioisotope seed was present in the contents of a given chamber and if the computer processor 30 determined that a radiation measurement should be acquired based upon the radiation sensing parameters as set by the user of the automated system 10. In this case, a message would be communicated from the automated motion control system 32 to the computer processor 30 when the radioisotope seed 110 was properly positioned indicating that a radiation measurement may be performed. Once a radiation measurement has been taken, or if no radiation measurement is required, the automated motion control system instructs the stepper motor 58 to move the push rod 62 forward to deliver the contents into the implant needle 130.

The trailing one of the position sensors 72 is provided along the path of material transfer to allow for detection of the leading edge of the contents with relation to the tip of push rod 62. As the contents of a given chamber 52 are moved by the position sensor 72, the total length of the contents may be determined. This allows for a verification of the length of the contents of a given chamber 52 with the information the automated system has about what should be in that chamber 52 to prevent potential misloads. In the event of an early or late activation of the sensor 72 by the tip of the push rod 62 in relation to the expected activation based on the anticipated length of the contents of that given chamber 52, an alarm or error message would be passed to the computer processor 30.

In the tip loading embodiment as shown in FIG. 9, as the contents are delivered into the implant needle 130, a stylet 134 that is preferably positioned in the implant needle 130 is pushed back by the advancing contents. In this way the needle 130 and stylet 134 are ready to use as soon as the loading process is completed and it is not necessary to insert a stylet into the implant needle after the loading process is completed, thereby incurring the risk that the stylet would dislodge the plug 116 or displace any of the loaded contents from the implant needle 130.

As any given implant needle 130 may be loaded from the contents of one or more chambers 52, it is important that the contents of a given chamber 52 containing a plug to be inserted at the tip 132 of implant needle 130 be accurately aligned with the end of the tip 132. In this case, the automated motion control system 32 preferably moves the contents of the chamber 52 containing a plug to an absolute location relative to the tip 132 of the implant needle 130, rather than moving the contents a relative distance based on the expected lengths of the contents of that chamber. In this way, the plugs 116 are always inserted so that they are flush with the ends of the tips 132 of the implant needles 130.

Figure 8:
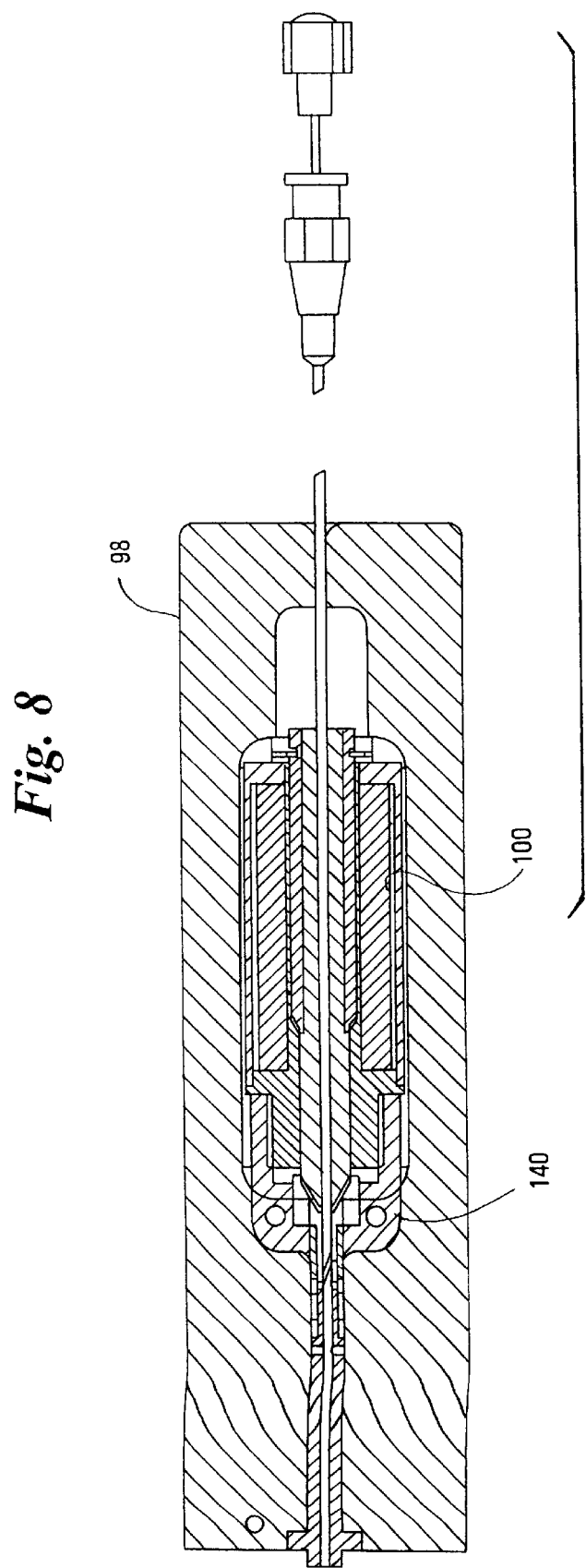
FIG. 8 is a detailed cross-sectional view of a tip alignment structure, radiation sensor and needle sensing system of the replaceable cartridge of FIG. 9.

Referring now to FIG. 8, an embodiment of the alignment structure 98 and the positioning of an implant needle 130 will be described. In order to begin a loading cycle, the needle tip 132 must be properly positioned by the user so that a known location is established for the needle tip 132. An optical sensor 140 is positioned precisely at the desired location of the needle tip 132 and is connected to the sensor circuitry 74 (FIG. 1). Preferably, the alignment structure 98 is beveled to match a beveling on the tip 132 of the implant needle 130. To accomplish proper alignment, the user inserts the implant needle 130 into the aperture 50 until it abuts alignment structure 98 and then rotates the implant needle 130 until the optical sensor 140 indicates proper alignment. Preferably, the optical sensor 140 remains active during the loading process to confirm that there is no movement of implant needle 130 during this process. Once the proper positioning of the implant needle 130 has been confirmed, an electrical solenoid 100 is activated to clamp the implant needle 130 in place relative to the cartridge 14. The force of the solenoid 100 is such that the implant needle 130 may not be moved during the loading operation, but not sufficient to crush the implant needle 130. In the preferred embodiment, the solenoid 100 is automatically released once the loading of the implant needle 130 is complete and a plug 116 has been inserted into the tip 132 of the implant needle 130.

Figure 10:
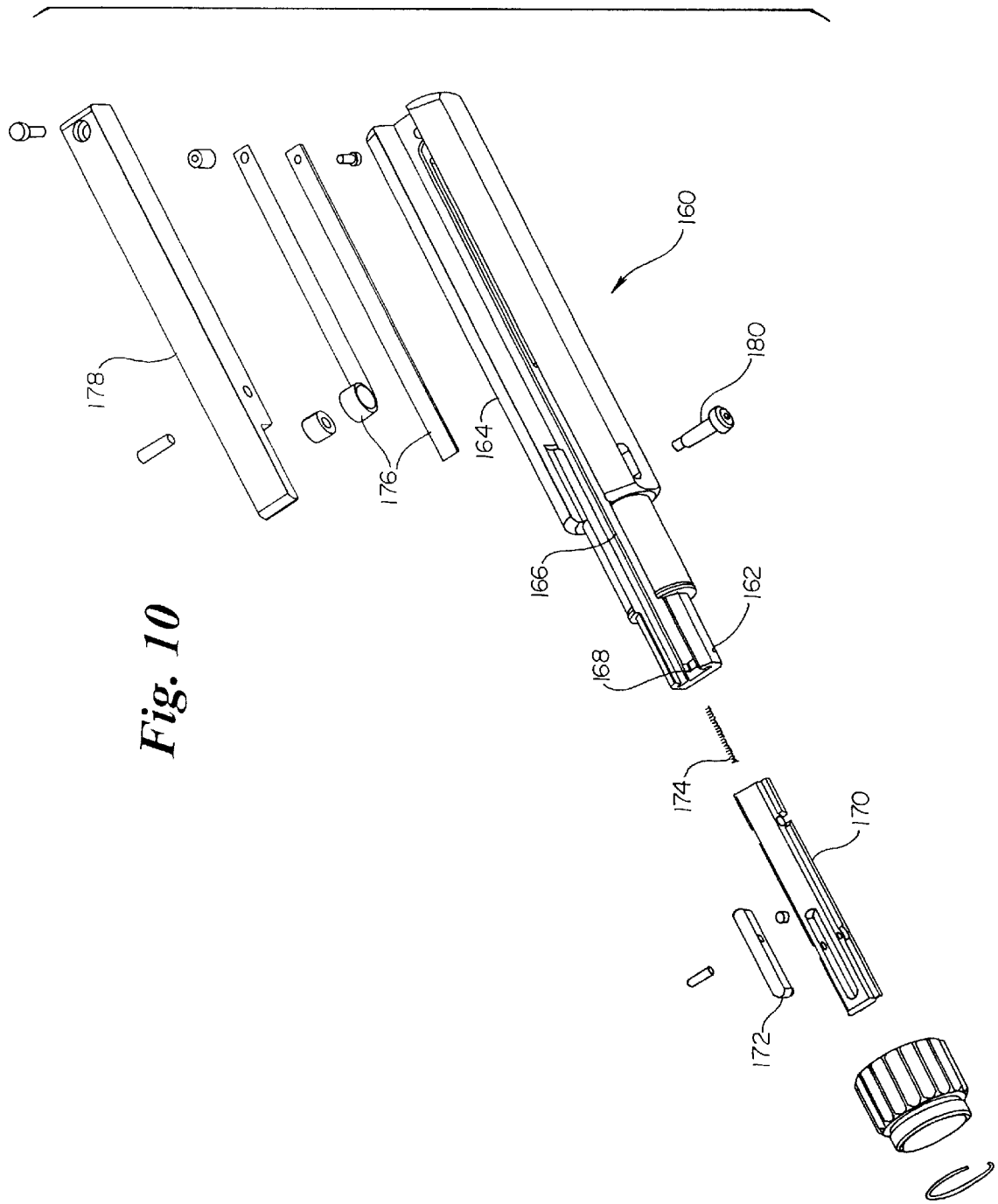
FIG. 10 is an exploded perspective view of a preferred embodiment of a loading clip in accordance with the present invention.
Figure 11:
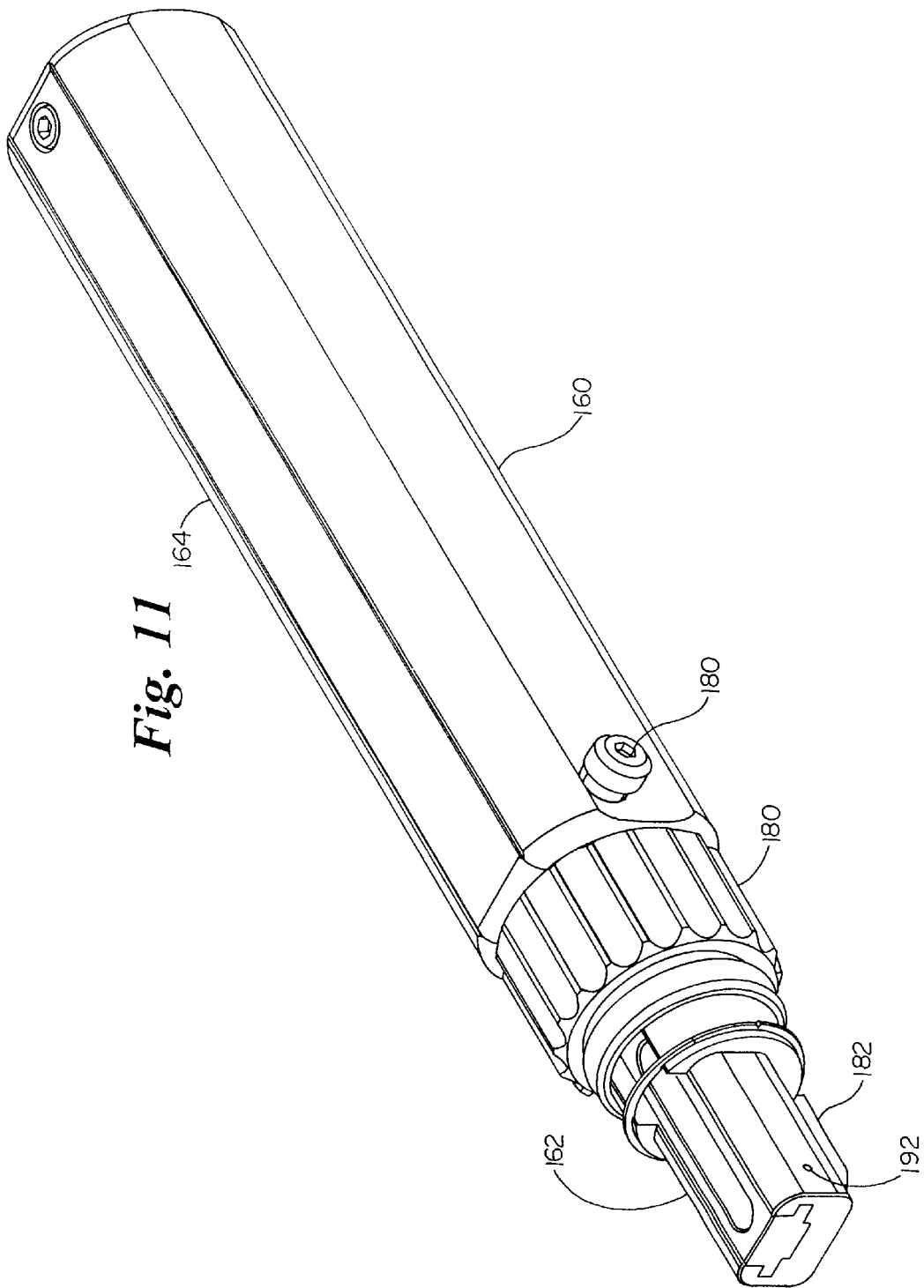
FIG. 11 is a perspective view of an assembled loading clip of FIG. 10.

Referring now to FIGS. 10 and 11, the embodiment of the present invention that includes a loading clip 160 will now be described. In one embodiment, the automated cartridge 14 can be preloaded at a factory and shipped for usage with radioisotope seeds inside. In another embodiment, the automated cartridge 14 includes a second aperture 150 rearward of the rotatable drum 54 along the line of travel of the push rod 62 through which radioisotope seeds are introduced into replaceable cartridge 14. Preferably, the second aperture 150 is covered by a loading clip cap 152 and includes screw based structure 154 or the like for securing the loading clip 160 onto the cartridge 14. As the seeds are loaded from the loading clip 160 into the replaceable cartridge 14, the push rod 62 is controlled to load the seeds one at a time into the chambers 52 in the drum 54. The loading clip 160 has structure 162 for mating with the second aperture 150 to introduce radioisotope seeds into the second aperture 150 one at a time.

Preferably, the loading clip 160 has a body 164 having a channel 166 defined therein, the channel 166 having a cavity 168 adapted for receiving a radioisotope seed at a distal end. A slider member 170 is slidably positioned within the channel 166 has a spring biased tooth 172 at a distal end. A spring 174 biases the slider member 170 toward the distal end of the body 164. A constant force spring member 176 is slidably positioned within the channel 166 between the slider member 170 and the body 164. A cover 178 secures the components within the channel 166. Radioisotope seeds are magazined into the loading clip 160 biased against the constant force spring member 176 by operation of a handle 180 on the slider member 170 which extends the tooth 172 over the cavity 168 and retracts a radioisotope seed in the cavity 168 into the channel 166. Preferably, the loading clip 160 is provided with a machine readable storage medium such as EEPROM 182 accessible via an electrical connector that stores indicia representing at least information about the radioisotope seeds located in the loading clip 160. A mating structure 190 preferably screws into the structure 154 on the cartridge 14.

In order to quickly load the loading clip 160, an aperture 192 near the cavity 168 parallel to the line of travel of the push rod 62 and parallel to the orientation of the channel 166 allows radioisotope seeds to be introduced into the cavity 168 as quickly as handle 180 can be activated. In one embodiment, this can be accomplished automatically under machine control of handle 180 and providing a continuous supply of radioisotope seeds connected to the aperture 192 in end-to-end fashion. Alternatively, the cavity 168 may be manually loaded with seeds one at a time using a tweezers, for example. In a preferred embodiment, the loading clip 160 is capable of loading up to sixty seeds and/or spacers. Preferably, one loading clip 160 will be loaded with seeds and a second loading clip 160 will be loaded with spacers. The computer processor 30 then loads the seeds from the first loading clip into the appropriate chambers 52 in the drum 54 in accordance with a predetermined dose plan. After the second loading clip 160 is mounted on the cartridge 14, the computer processor 30 directs the loading of the spacers into the appropriate chambers 52 in the drum 54 in accordance with a predetermined dose plan.

Although the cartridge 14 of the present invention has been described with respect to the automated station 10, it will be understood that the cartridge 14 of the present invention may also be used with other automated equipment as part of a low dose brachytherapy procedure. For example, the elongated member used to eject the radioisotope seeds in the preferred embodiment is a push rod 62 that loads the seeds into a plurality of implant needles. Where the cartridge 14 is used with an automated needle insertion system, the elongated member may be a trocar needle or similar cutting member that would first make an incision into the patient, then be withdrawn, and finally advanced through the aperture of the cartridge to eject the seeds.

Although the drum 64 has been described as the preferred embodiment of the positional member of the cartridge 14 with its movement controlled by stepper motor 56, it should be understood that other forms of this positional member and other motor arrangements would also work within the scope of the present invention. For example, the positionable member could be an X-Y grid of chambers with a pair of stepper motors used to drive the grid in X-Y directions to position the desired chamber in line with the aperture and push rod. 62. Although stepper motors, such as stepper motor 56, and encoders, such as encoder 58 are a convenient and economical manner of implementing the present invention so that it may be controlled by an external microprocessor arrangement, it will be recognized that other arrangements such as gears, drive belts and clutched motor shafts could be used in place of the stepper motor, and that contact sensors, optical sensors or registry from a known starting point could also be used in place of the encoder. It will also be seen that while the preferred embodiment interfaces with an external microprocessor, it would also be possible to incorporate a microprocessor into the cartridge itself and to communicate externally by telecommunications, radio communications or the like, instead of by electrical connectors.

For a more detailed description of the preferred embodiment of the radioisotope seed cartridge 14 and its preferred operation and loading, reference is made to the previously identified co-pending application entitled "RADIOISOTOPE SEED CARTRIDGE."

In the preferred embodiment, radiation in the form of x-rays from the radioisotope seeds 110 is detected by a radiation sensor 42 that is a LND zenon-filled proportional counter tube. This tube outputs pulses at a rate that is determined directly by the frequency of decay events and the pulse height is determined by the energy of the individual photons associated with each decay event. To quantify the radiation activity of a given source, all of the pulses having a height within a given band of interest are counted for a predetermined period and the rate is compared to a known reference. It will be understood that the particular requirements for positioning of a radioisotope seed 110 in front of the radiation sensor 42, such as positional tolerances or dwell time required for adequate measurement, may be different for different radiation sensors, and that trade-offs between the time required for radiation sensor readings and the accuracy of those readings may be made. Alternatively, it may be possible for certain radiation sensors 42 to take measurements while the radioisotope seeds 110 are moving by the radiation sensor 42, either at a normal rate of travel or perhaps at a reduced rate of travel. In another embodiment the push rod 62 is instructed to stop or slow down in front of the radiation sensor 42 for each item in the contents of the chamber 52 to verify that the contents are as expected (e.g., a spacer 112 registers no reading and a radioisotope seed 110 registers a reading). This type of verification can be quick and simple and would not require a complete characterization of the output of radiation sensor 42.

Figure 12:
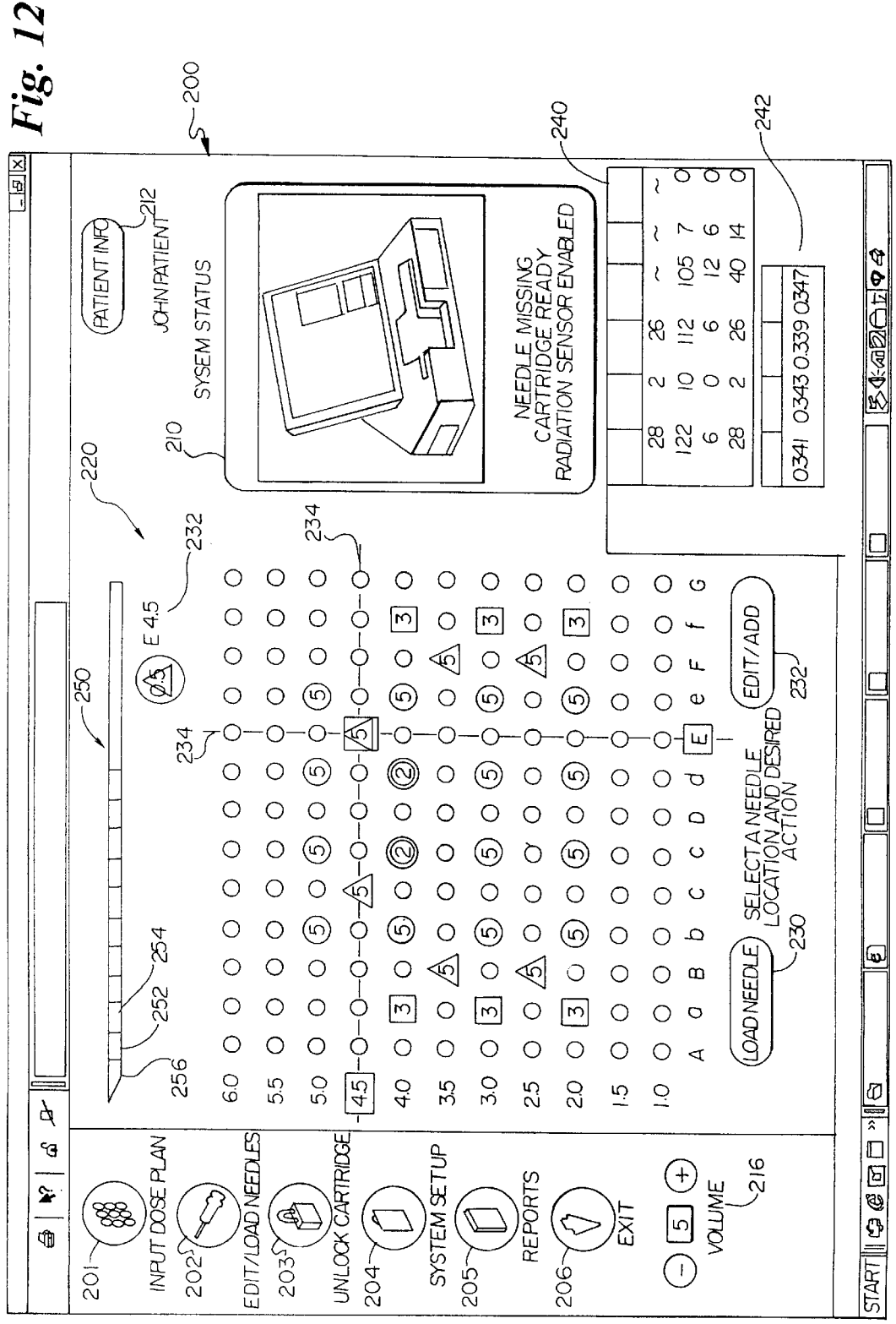
FIGS. 12 and 13 are graphic depictions of a preferred embodiment of a user interface screen of a display of the automated system of FIG. 1.
Figure 13:
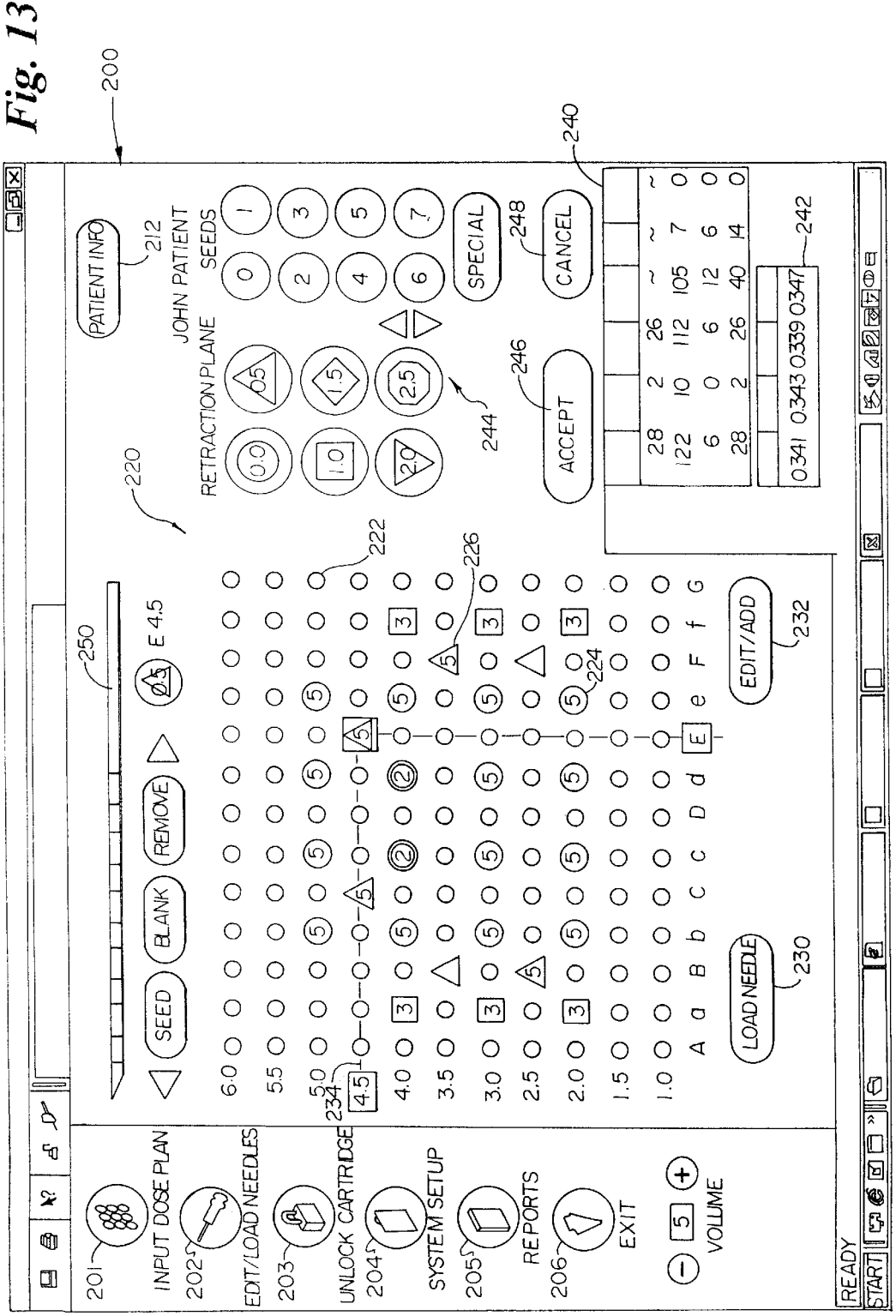

Referring now to FIGS. 12 and 13, a preferred embodiment of the user interface 200 as presented on display 40 (FIG. 1) will now be described. Preferably, the display 40 is a touch screen display and the computer processor 30 utilizes a Windows® NT operating system with a Radisys® In Time environment. To a user, however, the user interface 200 preferably appears as a dedicated virtual machine having a single primary touch-screen user screen as shown in FIG. 7. Although the preferred embodiment of the present invention will be described in connection with a touch-screen user interface 200, it will be recognized that various other user interfaces, such as conventional video displays, LCD displays or specialized displays may also be used with the present invention. In addition, it would be possible to provide for an audio-controlled user interface coupled with an optional display screen to allow for voice-activated control of the loading process.

In the preferred embodiment of user interface 200, a series of dedicated touch-activated buttons 201 to 206 are positioned to always remain visible on the left side of the display. The user interface 200 is preferably designed to provide a very flat icon-based menu structure with minimal overlay windows where all of the functions controlled by a user are accessible though each touch screen inputs. A virtual keyboard may be selected to enter alphanumeric data. Alternatively, a mouse and keyboard may be connected to the computer processor 30 to enter such data. Another equivalent input device is a joy stick or game port pad or equivalent pointing/directional input device. Preferably, each of the buttons 201–206 has an icon on the top half of the button and a corresponding text message on the bottom half of the button. A status icon 210 is preferably displayed along the leftof user interface 200 to display status messages such as Cartridge Detected, Reading Inventory, Running Diagnostics, Verifying Radiation Sensors, Cartridge Ready, Printing and the like. Once a cartridge 14 has been successfully loaded and locked into the cartridge receiving structure 16, at least the patient name information from the EEPROM 79 of that cartridge 14 is displayed in the top left corner of the user interface 200. Additional patient information can be accessed through button 212. In a preferred embodiment, the system status area 210 is also used as a multi-media help screen that can display information about using the system 10, as well as general information about the particular brachytherapy procedure to be performed. A volume control 216 is provided to conveniently control the audio volume of multi-media information displayed on the status area 210.

The primary display in the main part of the user display 200 is the loading pattern grid 220 which replicates an interactive grid of how the implant needles 130 are to be loaded in a format that is similar to the paper format currently used for prostate cancer brachytherapy procedures. In this format, the numbers along the left side of grid 220 represent the height in centimeters and the letters represent the width in 0.5 centimeter increments (1.0 centimeters between capital letters) of the locations where the implant needles 130 are to be inserted from a reference base axis that would be located at 0.0. The open circle icons 222 at the intersection of each of these coordinates represents a chamber in an implant grid that is used to implant the series of implant needles 130. Each of the icons 224, 226, 228 in the center of grid 220 represent an implant needle 130 with the number in the center of the icons 224, 226, 228 indicating the number of radioisotope seeds 110 that are planned for that implant needle 130. The icons 224 are for needles in which the seeds 110 are spaced at regular intervals using full-length spacers 112. The icons 226 are for needles in which the seeds 110 are spaced at regular intervals, but are offset or staggered by using at least one partial-length spacer 114. Icons 228 represent those needles in which the seeds 110 are not spaced at regular intervals due to the staggering of partial length spacers 114 and full length spacers 112.

The grid 220 is active as shown in FIG. 13 when the Edit/Add Needles button 232 is activated. The currently active location is indicated by the message 232 at the upper left corner of the grid 170 and by the intersecting lines 234 that highlight that coordinate in the grid. A user selects a different currently active needle location by pointing to that location. In one embodiment, the status of each of the icons 224, 226 and 228 are conveniently shown in the colors as indicated in the scoreboard area 240. The scoreboard area 240 is dynamically updated by the computer 30 to reflect the planned, loaded, not yet loaded, cartridge inventory, extras and discards that the user has available or has used. A radiation reading area 242 displays the information generated by radiation sensor 42. The Edit control area 244 allows a user to select retraction plane depths and number of seeds for the active needle location. Once the desired configuration is selected, the user accepts the configuration for the active needle location by entering button 246. Alternatively, the information for this location can be discarded by selecting the cancel button 248.

Once a user activates the Load Needle button 230 as shown in FIG. 12, the user is instructed to insert an implant needle to be loaded by the system status message 210 at the left of the user interface 200. When an implant needle 130 is detected in the aperture 50, an icon 250 representing the needle 130 is displayed at the top of the user interface 200. In the tip loading embodiment, this icon is interactive in response to the orientation and alignment of needle 130 as detected by optical sensor 134 as previously described. For example, the orientation of the beveled end 254 of icon 252 could rotate until alignment was achieved, at which time the color of the icon 252 would change from a red background to a green background and a text message in the system status area 210 that the needle was present and locked would also be displayed. As the implant needle 130 is being loaded, position indicators 252 and 254 in the needle icon 250 represent locations in the implant needle in which radioisotopes 110 and spacers 112, 114 may be loaded. As the loading process progresses, seed icons 252 and spacer icons 254 are displayed in the respective position indicators where those items are positioned in the implant needle 130. In the case of the tip loading embodiment, once a plug 116 is inserted at the tip 132 of implant needle 130, a plug icon 156 is displayed at the end position indicator and the icon 250 would change to a white background while the system status area 210 would be changed to indicate that the implant needle 130 was now loaded and could be removed. At this point, the computer processor 30 would instruct the solenoid 100 to unlock the implant needle 130.

The Input Dose Plan button 201 allows a user to input a predetermined dose plan. Two input options are provided, a Manual Input option and a Load File option. In the Manual Input option, the grid 220 is displayed with no predetermined dose plan overlayed. In this mode, the user would select a desired location and then use the Edit/Load Needle button 202 to indicate how the implant needle 130 corresponding to that location should be filled. This process would then be repeated for each implant needle to be loaded via this manual option. In the Load File option, a pop-up window is displayed showing the default dose plan that was used to generate the configuration of contents of the particular cartridge 14. In a preferred embodiment, a compact disc (CD) is delivered along with the cartridge 14 to the hospital where the procedure is to be performed and the default dose plan is contained on this CD and is read by the CD player 38. In another embodiment, a compressed version of the default dose plan is stored on the EEPROM 79 in the cartridge 14. If the automated system 10 was used during the generation of the dose plan at an initial planning visit or at the time of the procedure, then the dose plan would be stored on the hard drive 34. Alternatively, the default dose plan could be stored on a floppy disc and read by the floppy disc drive 36 or could even be stored on a remote location and accessed by an external interface, such as by an encoded transmission over the Internet or over a private dial-up network. If the user desires to override the default dose plan and select another dose plan, the pop-up window would allow the user to search the various drives accessible by the automated station to locate an appropriate dose plan file. Preferably, the default dose plan is stored in a proprietary text file format adapted for use by the software running on the computer processor 30. Alternatively, the computer processor 30 could translate the output files of any of a number of dose planning software packages to the proprietary text file format as part of the process of loading the dose plan. Once an appropriate file has been selected, the user can load the selected file as the dose plan and the details of that dose plan are then displayed on the user interface 200. Alternatively, the computer processor 30 could be provided with the dosimetry software package and a user could develop the dose plan directly on the computer processor 30 either prior to the procedure or during the procedure. For example, the dose plan could be modified as the procedure progresses in response to needles that have been loaded. In this embodiment, a common file structure could be shared between the dosimetry software and the control software running on the computer processor 30 for controlling loading of the needle 130.

The Unlock Cartridge button 203 is used to instruct the automated system to initiate the process of preparing for the cartridge 14 to be removed from the cartridge receiving structure 16. Various checks are performed by the computer processor 30 to insure that certain tasks are completed. These tasks include confirmation that no implant needles are in the cartridge, a verification that the current inventory of the seeds 110 in the drum 54 is stored in EEPROM 79, a homing function for the push rod 62 into an empty chamber 52 in drum 54 to lock the drum 54 into position. After these tasks are completed, power would be shut off to the cartridge 14 and the solenoid 26 is deactivated to unlock the cartridge. A pop-up message is displayed to the user instructing them to manually remove the cartridge 14 from the cartridge receiving structure 16 and providing for an option to cancel this operation. Preferably, a countdown timer is shown during which time the user would be able to manually remove the cartridge 14 and after which the solenoid 26 would be engaged again to relock the cartridge 14 in place. The contact on the electrical connector 28 is monitored to confirm that the cartridge 14 has been removed and the pop-up windows are closed once the cartridge 14 has been removed.

The System Setting button 204 allows the user to view and edit various parameters of the automated system 10, including radiation measurement parameters, radiation calibration settings, motion control parameters and display preferences. In the case of radiation measurement parameters, the user is preferably given the option in a set-up window of choosing to monitor (i) all contents, (ii) all seeds, (iii) every given number of seeds, or (iv) only the first seed in each implant needle. Optionally, the estimated time required to load an average implant needle at each setting can also be displayed. The radiation calibration settings would also have a set-up window that would take a user through the process of testing the radiation sensor 42 by inserting a radiation source of a known intensity into the aperture 50 and positioning that source in front of the radiation sensor 42.

The Reports button 205 allows the user to print out certain predetermined reports for the automated system 10, including a loading plan report, a radiation reading/calibration report, a case summary and a system diagnostic report. These reports may be printed directly over the external connections for computer processor 30, may be stored to a file for later printing or review. The user may be provided with certain formatting preferences and printing options to customize certain details of the presentation of these reports.

The Exit button 206 allows the user to exit or switch from the needle loading application software back to the operating system software running on the computer processor 30. This button 206 can either be conditioned on a proper shutting down of the automated system 10, including removal of the cartridge 14, or it can allow for an option to switch to another application that could be running on computer processor 30. In one embodiment of the present invention, the computer processor 30 is provided with dose planning software that would be used by the physician to create the predetermined dose plan that is to be used by the needle loading application software.

In another embodiment, the computer processor 30 is provided with dose planning software and with image management software that can capture ultrasound images from a rectal ultrasound probe (not shown). In this embodiment, the motherboard of the computer processor 30 is provided with a frame-grabber daughter board 33 (as shown in FIG. 1B) that interfaces with the ultrasound probe to obtain frame-by-frame image of the prostate gland as the probe is advanced. Preferably, a linear stepper motor is coupled to the probe and to the automated motion control system 32 to allow the image management software to control the movement of the probe. In this way, precise control of the frame-by-frame images used for the volume study can be obtained and the dose plan generated as a result of the volume study can be correlated back to the frame-by-frame images. Preferably, the probe is operated in a similar manner at the time of the brachytherapy procedure and the frame-by-frame images of the volume study can be compared with the current images of the prostate gland. A matching or registration of these two different sets of images can be done manually or with the assistance of the computer processor 30. Once the matching is complete, the dose planning software can compare any changes in the volume or positioning of the prostrate gland and update the recommended dose plan accordingly. In this embodiment, as in the preferred embodiment, the number and combination of radioisotope seeds and spacers preloaded into the cartridge 14 can be increased by a given percentage over the minimum number required by the predetermined dose plan to allow for changes to the dose plan as a result of changes to the volume and position of the prostate gland that may occur between the time of the volume study and the time of the brachytherapy procedure. In this embodiment, the physician would utilize the display 40 of the automated system as the display for conducting the volume study and monitoring the brachytherapy procedure, as well as for controlling the automatic loading of the implant needles.

Figure 14:
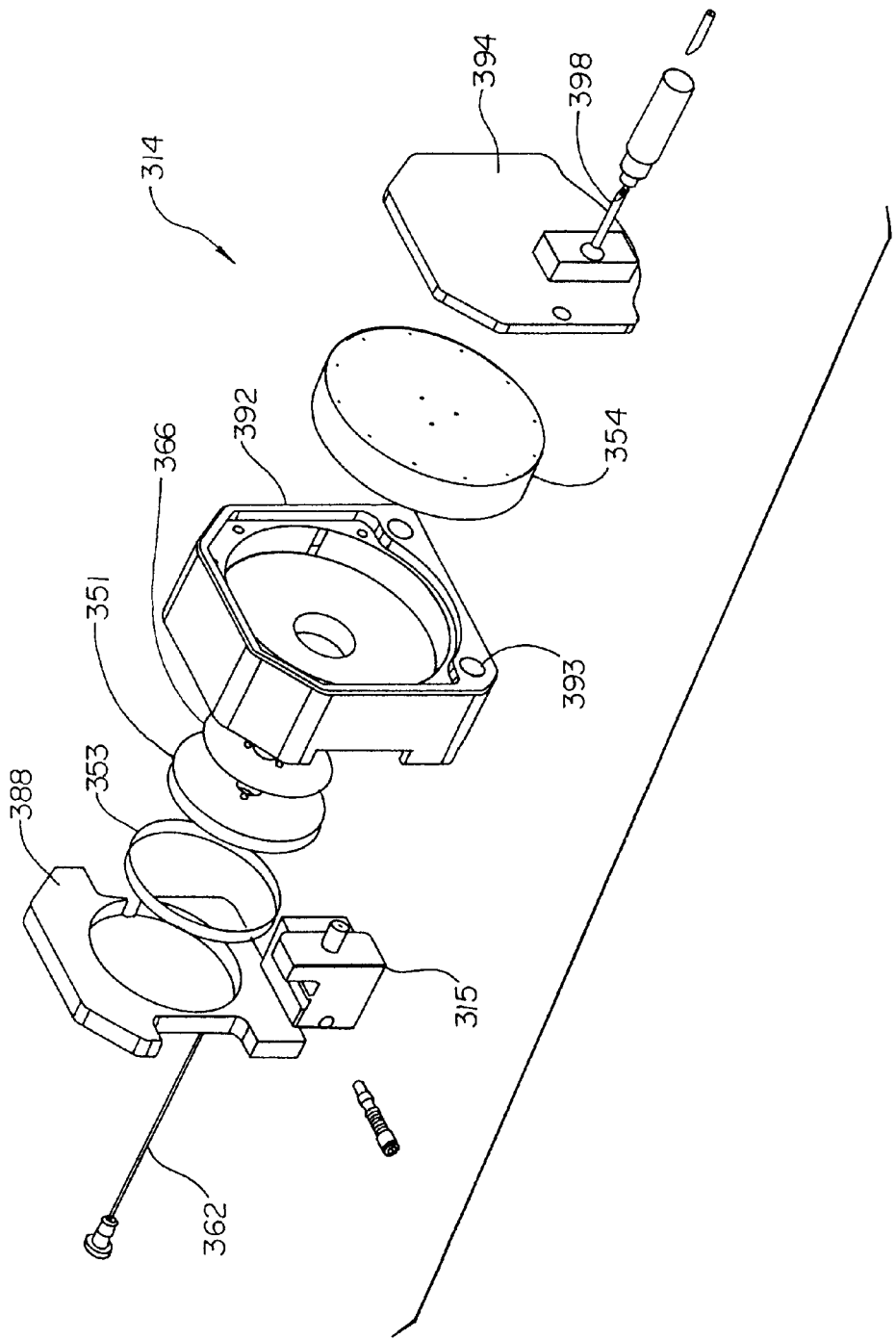
FIGS. 14 and 15 is a perspective of another embodiment of the automated system of the present invention having a replaceable cartridge that does not include the stepper motors.
Figure 15:
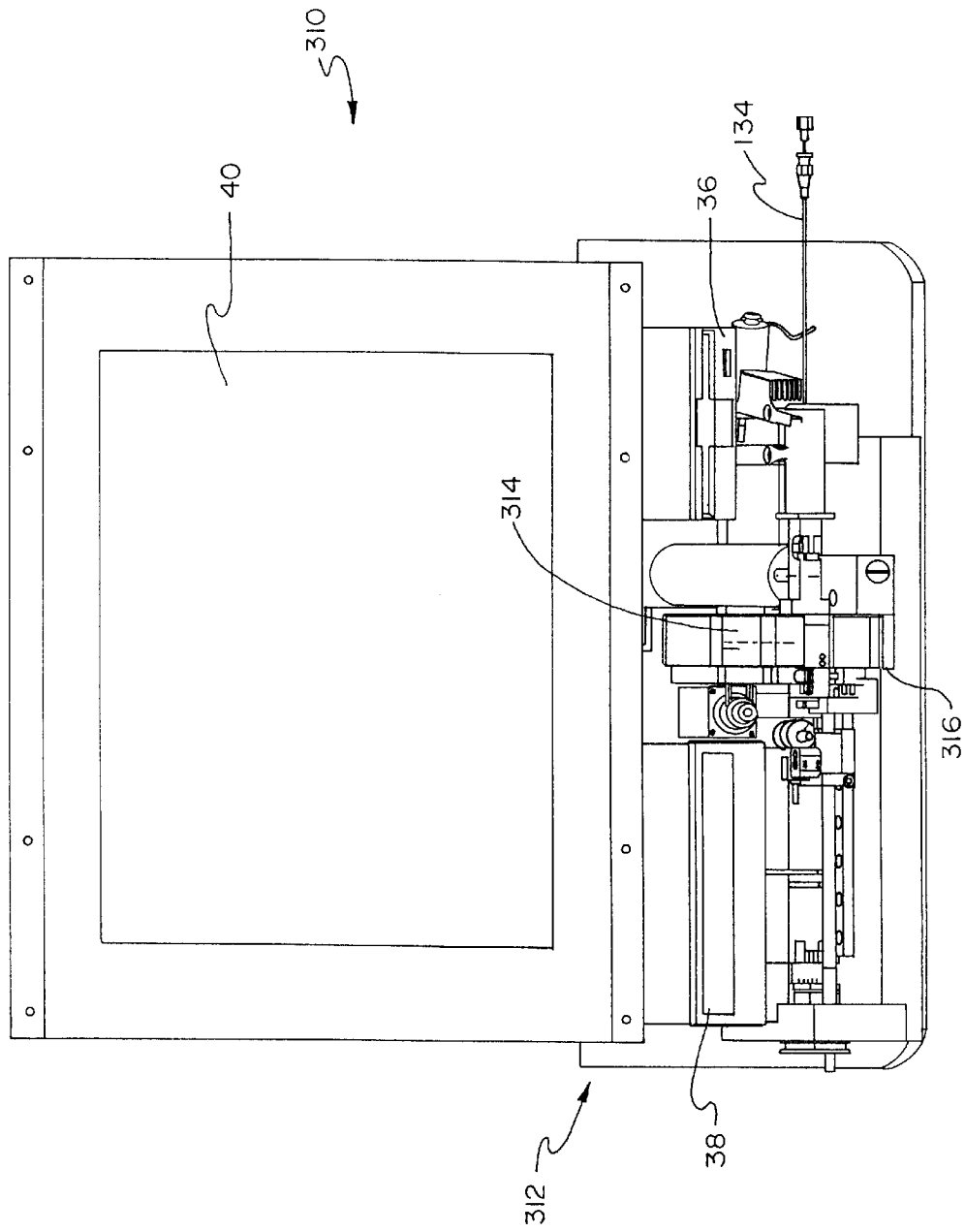

Referring now to FIGS. 14 and 15, an alternate embodiment of an automated system 310 for loading low dose radioisotope seeds into a plurality of implant needles is comprised of a loading station 312 into which a replaceable cartridge 314 may be positioned. It will be understand that the description of corresponding items in the automated system 310 is similar to the preferred embodiment of the automated system 10 unless otherwise noted. The cartridge 314 does not have any internal stepper motors, but rather interfaces a drive motor 356 in the loading station with a drive wheel 357 in the rotatable drum 352. The cartridge 314 is held in place by a position registration mechanism 317 that comprises a ball and detent mechanism with the cartridge having at least one detent defined on an outer surface and the loading station 312 having a cam driven ball mechanism which selectively seats at least one ball in the at least one detent to properly register the position the cartridge 314 within the cartridge receiving structure 316. An external push rod 362 is carried by a guide rail 363 and is driven by a linear actuator 360 that is contained in the loading station 312, rather than in the cartridge 314. Unlike the cartridge receiving structure 16 of the automated system 10, the cartridge receiving structure 316 of the alternate embodiment of the automated system 310 is designed for front horizontally-oriented loading and includes a hinged door 317 that functions as a tray to collect any seeds or spacers that may spill out of the cartridge 314. This can occur because a manually operated port 315 is provided in the cartridge 314 that allows a user to individually access and load seeds and spacers in a manual manner by disengaging the linear actuator 360 and operating the push rod 362 manually. When the cartridge 314 is in position in the cartridge receiving structure 316, a first drive wheel 351 preferably having a rubber ring 353 and a position encoder 366 in the cartridge 314 are operably engaged by a second drive wheel 352 and a position sensor 364 in the loading station 312 to drive and sense the position of the rotatable drum 354 in the cartridge 314. A position registration mechanism 353 preferably positions the cartridge within the cartridge receiving structure within the tolerance of +/−0.010 inches. Preferably, the position registration mechanism 393 comprises a ball and detent mechanism with cartridge 314 having at least one detent defined on our surface and loading station 312 having a cam driven ball mechanism that selectively seats at least one ball in the least one detent to properly register the position of the cartridge 314 within the cartridge receiving structure 316. The loading station also includes at least one guide rail 361 having a push rod 362 connected to a linear actuator 360 that is controlled by the automated motion control system 332 to selectively eject the radioisotope seeds and spacers from the periphery of the rotatable drum 354 of the cartridge 314. In this embodiment, the encoder disc 366 for the rotatable drum 352 is part of the cartridge 314, but the encoder circuitry and position sensor 364 for the rotatable drum 352 and the encoder disc 370 and encoder circuitry 368 for the linear actuator 360 are part of the loading station 312. An EEPROM 399 that functions in a manner similar to the EEPROM 104 is part of the cartridge 314, although the design and interface of this EEPROM 339 are configured such that it is easily removed from the cartridge 314 or is encased so as to allow the cartridge 314 to be sterilized without the need to disassemble parts of the cartridge 314. Thus, while there are more critical mechanical tolerances that must be maintained in this embodiment, such as the interface between the optical encoder disc 366 and the position sensor 364, there are fewer electrical connections and less expense in the cartridge 314. In addition, disassembly of the cartridge 314 is not necessarily required in order for the device to be sterilized.

In another alternate embodiment of an automated system 10 for loading low dose radioisotope seeds into a plurality of implant needles multiple replaceable cartridges may be utilized in place of the single repleaceable cartridge 12. For example, one cartridge could only contains radioisotope seeds and another cartridge couldcontains material for spacers and plugs, although separate cartridges for each is also contemplated. Multiple cartridges may be configured like cartridge 14 having internal stepper motors and circuitry, or may be configured like cartridge 314 having external stepper motors and circuitry. The advantage of multiple cartridges is that a smaller rotatable drum may be utilized for each cartridge, thereby increasing the indexing speed and the separation of seeds and spacers into separate cartridges can simplify the combinatorial arrangements of seeds and spacers. Preferably, the cartridges would be positioned in longitudinal sequential order relative to the path of travel of the push rod such that a seed and spacer are loaded together from the multiple cartridges on a single pass of the push rod. A separate third cartridge could contain a plurality of plugs. Alternatively, instead of providing individual spacers, one of the cartridges could supply a source of material from which the loading station creates spacers and/or plugs to be selectively ejected by the automated motion control system into each of the needles. Because the spacers and plugs are made of relatively long lasting material such as suture or polymer material, this embodiment allows for a source of the material for the spacers or plugs to be supplied separately from supply of the time critical radioisotope seeds. In the case of the spacers, for example, it would be possible to provide a continuous coil of suture material as part of a replaceable cartridge with mechanisms to dispense and cut the appropriate lengths of suture material as part of a replaceable cartridge or loading station. Alternatively, a replaceable cartridge or compartment in loading station may be loaded with a bulk quantity of plugs that are oriented and advanced into the proper positioning by mechanisms within the loading station. In another alternate embodiment the number of cartridges is made equal to the greatest number of radioisotope seeds to be loaded into a single implant needle such that all of the seeds and spacers for a single needle could be simultaneously loaded on a single pass of the push rod. In another alternate embodiment, multiple push rods could be used with the multiple cartridges having multiple apertures to load multiple needles at the same time. While it is not likely that parallel processing of the loading of multiple needles would be required to keep up with a physician implanting the needles in a patient, this embodiment could significantly reduce the time required to load an entire set of needles for a given procedure where the needles are loaded in advance.

It should be understood that in the broadest sense, the automated motion control system of the present invention encompasses the various motors, actuators, encoders, detectors and feedback circuits that accomplish the controlled motion required to load the implant needles automatically and without manual intervention. It will be recognized by a person of ordinary skill in the art that numerous variations in the arrangement of motors, actuators, encoders, detectors and feedback circuits can be made and still accomplish the function of loading the implant needles automatically, such as belt driven systems or screw-drive powered systems instead of direct motor driven systems, mechanical or electrical encoders and detectors instead of optical encoders and detectors, and linear actuators instead of rotary actuators or vice versa.

Although the preferred embodiment of the automated system of the present invention has been described, it will be recognized that numerous changes and variations can be made and that the scope of the present invention is intended to be defined by the claims.

What is claimed is:

1. An automated system for loading low dose radioisotope seeds into a plurality of implant needles comprising:

a single drop-in, enclosed replaceable cartridge containing a plurality of radioisotope seeds and a plurality of spacers preloaded into the cartridge, the cartridge having at least one aperture; and a loading station having structure defining a drop-in cartridge receiving structure including an automated motion control system that selectively ejects radioisotope seeds and spacers from the at least one aperture of the cartridge into each of a plurality of implant needles when the cartridge is positioned in the cartridge receiving structure and each of the plurality of implant needles is positioned relative to the at least one aperture of the cartridge so as to receive the selectively ejected radioisotopes seeds and spacers within the implant needle.

2. The automated system of claim 1 wherein the plurality of implant needles are positioned relative to the at least one aperture of the cartridge one implant needle at a time and the automated motion control system selectively ejects the radioisotope seeds and spacers into the plurality of implant needles one implant needle at a time.

3. The automated system of claim 1 wherein the cartridge includes structure to secure a rear of a needle and the spacers and seeds are selectively ejected into the rear of the needle.

4. The automated system of claim 1 wherein the loading station includes a front side oriented toward a user and wherein the cartridge receiving structure is defined in the front side and the plurality of implant needles are positioned in the loading station oriented parallel to the front side.

5. The automated system of claim 1 wherein the cartridge receiving structure defines a downwardly angled path of travel for inserting the cartridge into the cartridge receiving structure.

6. The automated system of claim 1 wherein the cartridge disengageably mates with the cartridge receiving structure of the loading station within a mechanical tolerance of +/−0.010 inches.

7. The automated system of claim 1 wherein the loading station further includes a solenoid that selectively locks the cartridge in place when the cartridge is positioned in the cartridge receiving structure.

8. An automated system for loading low dose radioisotope seeds into a plurality of implant needles comprising:

a cartridge containing a plurality of radioisotope seeds and a plurality of spacers preloaded into the cartridge, wherein the cartridge includes a single rotatable drum and wherein the plurality of radioisotope seeds and the plurality of spacers are preloaded into apertures spaced around the periphery of the rotatable drum, the cartridge having at least one aperture; and a loading station having structure defining a cartridge receiving structure and including an automated motion control system that selectively ejects radioisotope seeds and spacers from the at least one aperture of the cartridge into each of a plurality of implant needles when the cartridge is positioned in the cartridge receiving structure and each of the plurality of implant needles is positioned relative to the at least one aperture of the cartridge so as to receive the selectively ejected radioisotopes seeds and spacers within the implant needle.

9. The automated system of claim 8 wherein the cartridge further includes a pair of stepper motors, a first stepper motor to drive the rotatable drum and a second stepper motor to drive a capstan assembly that operably drives a push rod along a line of travel through a selectively indexed one of the apertures spaced around the periphery of the rotatable drum, and wherein the rotatable drum has an associated encoder and related circuitry that provide a positional feedback signal to the automated motion control system to control the stepper motor.

10. The automated system of claim 8 wherein the cartridge receiving structure defines a downwardly angled path of travel for inserting the cartridge into the cartridge receiving structure.

11. The automated system of claim 8 wherein the cartridge releasably mates with the cartridge receiving structure of the loading station within a mechanical tolerance of +/−0.010 inches.

12. The automated system of claim 8 wherein the loading station further includes a solenoid that selectively locks the cartridge in place when the cartridge is positioned in the cartridge receiving structure.

13. An automated system for loading low dose radioisotope seeds into an implant needle comprising:
   at least one source of a plurality of radioisotope seeds, a plurality of spacers and a plurality of plugs to be selectively ejected from at least one aperture;
   structure for holding a tip of an implant needle in a position relative to the at least one aperture; and
   an automated motion control system that selectively ejects radioisotope seeds and spacers from the at least one aperture into the tip of the implant needle and selectively positions one of the plurality of plugs in the tip of the implant needle after the radioisotope seeds and spacers have been ejected into the tip of the implant needle to hold the radioisotope seeds and spacers in place in the implant needle.

14. The automated system of claim 13 wherein the at least one source comprises at least one replaceable cartridge received in a cartridge receiving structure defined in a loading station that houses the automated motion control system.

15. An automated system for loading low dose radioisotope seeds into an implant needle comprising:
   a cartridge containing at least a plurality of radioisotope seeds preloaded into the cartridge, the cartridge having at least one aperture and containing a machine readable storage medium that stores indicia representing at least the quantity of the plurality of radioisotope seeds preloaded into the cartridge; and
   a loading station having structure defining a cartridge receiving structure and including a computer processor that accesses the machine readable storage medium and utilizes the indicia stored therein to control an automated motion control system that selectively ejects radioisotope seeds from the at least one aperture of the cartridge into the implant needle when the cartridge is positioned in the cartridge receiving structure and the implant needles is positioned relative to the at least one aperture of the cartridge so as to receive the selectively ejected radioisotopes seeds within the implant needle.

16. The automated system of claim 15 wherein the machine readable storage medium comprises an electrically erasable programmable read-only memory (EEPROM) accessible to the loading station via an electrical connector.

17. The automated system of claim 15 wherein the computer system is provided with a machine readable medium that stores at least a predetermined dose plan and the computer processor controls the automated motion control system to selectively eject radioisotope seeds into the implant needle in accordance with the predetermined dose plan.

18. An automated system for loading low dose radioisotope seeds into an implant needle comprising:
   at least one source of a plurality of radioisotope seeds to be selectively ejected from at least one aperture;
   a loading station operably connected to the at least one source and including an automated motion control system that selectively ejects radioisotope seeds from the at least one aperture into the implant needle using a push rod; and
   at least one position sensor operably connected to the automated motion control system and positioned in a line of travel of the push rod to detect movement of the push rod.

19. The automated system of claim 18 wherein the at least one source comprises at least one replaceable cartridge received in a cartridge receiving structure defined in a loading station that houses the automated motion control system.

20. A method for loading low dose radioisotope seeds into a plurality of implant needles comprising:
   (a) providing a plurality of radioisotope seeds and a plurality of spacers;
   (b) using an automated motion control system to move a straight push rod to selectively eject radioisotope seeds and spacers into each of a plurality of implant needles from at least one aperture when each of the plurality of implant needles is positioned relative to the at least one aperture so as to receive the selectively ejected radioisotope seeds and spacers with the implant needle.

21. A The method of claim 20 wherein step (a) is accomplished by providing a replaceable cartridge containing the plurality of radioisotope seeds that is housed in a cartridge receiving structure defined in a loading station that houses the automated motion control system used in step (b).

22. The method of claim 20 wherein step (b) selectively ejects the radioisotope seeds and spacers into a rear of each of the plurality of implant needles.

23. The method of claim 21 wherein step (a) is performed by inserting the cartridge into the cartridge receiving structure along a downwardly angled path of travel defined by the cartridge receiving structure.

24. The method of claim 21 wherein step (a) is performed such that the cartridge disengageably mates with the cartridge receiving structure of the loading station within a mechanical tolerance of +/−0.010 inches.

25. The method of claim 21 wherein the loading station further includes a solenoid and the automated control system in step (b) selectively locks the cartridge in place utilizing the solenoid when the cartridge is positioned in the cartridge receiving structure.

26. The method of claims wherein step (b) is performed such that the plurality of implant needles are positioned relative to the at least one aperture one implant needle at a time and wherein the automated motion control system selectively ejects the radioisotope seeds and spacers into the plurality of implant needles one implant needle at a time.

27. The method of claim 20 wherein step (b) further comprises:
   sensing a proper positioning of the implant needle relative to the at least one aperture.

28. A method for loading low dose radioisotope seeds into a plurality of implant needles comprising:
   (a) providing a plurality of radioisotope seeds and a plurality of spacers;
   (b) using an automated motion control system to selectively eject radioisotope seeds and spacers into each of a plurality of implant needles from at least one aperture when each of the plurality of implant needles is positioned relative to the at least one aperture so as to receive the selectively ejected radioisotopes seeds and spacers into a tip of each of the plurality of implant needles.

29. The method of claim 28 further comprising:
(c) providing a plurality of plugs; and
(d) using the automated motion control system to selectively position one of the plurality of plugs in the tip of the implant needle after the radioisotope seeds and spacers have been ejected into the tip of the implant needle to hold the radioisotope seeds and spacers in place in the implant needle.

30. The method of claim 28 wherein step (b) further comprises:
aligning the tip of the implant needle relative to the at least one aperture of the cartridge.

31. A method for loading low dose radioisotope seeds into a plurality of implant needles comprising:
(a) providing a plurality of radioisotope seeds and a plurality of spacers in a cartridge having a machine readable storage medium that stores indicia representing at least the quantity and location of the plurality of radioisotope seeds preloaded into the cartridge; and
(b) using an automated motion control system having a computer processor and a machine readable medium that stores at least a predetermined dose plan to selectively eject radioisotope seeds and spacers from the cartridge into each of a plurality of implant needles wherein the computer processor controls the automated motion control system to selectively eject radioisotope seeds from the cartridge in response to the indicia and the predetermined dose plan.

32. An automated system for loading low dose radioisotope seeds into a plurality of implant needles comprising:
a cartridge assembly containing a plurality of radioisotope seeds and a plurality of spacers preloaded into the cartridge and having at least one aperture, the cartridge assembly housing:
at least one rotatable drum having a plurality of radioisotope seeds and a plurality of spacers preloaded into apertures in the at least one rotatable drum;
a first stepper motor to drive the at least one rotatable drum; and
an associated encoder for the at least one rotatable drum and related circuitry that provide a positional feedback signal; and
a loading station having structure including an automated motion control system that selectively ejects radioisotope seeds and spacers from the at least one aperture of the cartridge assembly into each of a plurality of implant needles when each of the plurality of implant needles is positioned relative to the at least one aperture of the cartridge assembly by controlling the first stepper motor in response to the positional feedback signal from the associated encoder.

33. The automated system of claim 32 wherein the cartridge assembly further houses:
a second stepper motor that operably drives a pushing member along a line of travel through a selectively indexed one of the apertures in the at least one rotatable drums.

34. The automated system of claim 32 wherein the cartridge assembly includes a single rotatable drum containing both the seeds and the spacers in apertures defined in the periphery of the single rotatable drum.

* * * * *